(12) United States Patent
Chen et al.

(10) Patent No.: US 6,248,528 B1
(45) Date of Patent: Jun. 19, 2001

(54) METHODS AND COMPOSITIONS FOR THE DIAGNOSIS AND TREATMENT OF NEUROPSYCHIATRIC DISORDERS

(75) Inventors: Hong Chen, Brookline, MA (US); Nelson B. Freimer, San Francisco, CA (US)

(73) Assignees: Millennium Pharmaceuticals, Inc., Cambridge, MA (US); Regents of the University of California, Oakland, CA (US)

(*) Notice: Subject to any disclaimer, the term of this patent is extended or adjusted under 35 U.S.C. 154(b) by 0 days.

(21) Appl. No.: 09/285,601

(22) Filed: Apr. 2, 1999

Related U.S. Application Data

(60) Provisional application No. 60/080,841, filed on Apr. 6, 1998.

(51) Int. Cl.[7] .............................. C12Q 1/68; C07H 21/02
(52) U.S. Cl. .............................................. 435/6; 536/23.5
(58) Field of Search ........................ 435/7.71, 6; 536/23.5

(56) References Cited

U.S. PATENT DOCUMENTS

| | | |
|---|---|---|
| 5,075,217 | 12/1991 | Weber . |
| 5,364,759 | 11/1994 | Caskey . |

FOREIGN PATENT DOCUMENTS

WO 89/10134   11/1989   (WO) .

OTHER PUBLICATIONS

Baron et al., 1993, "Diminished Support for Linkage between Manic Depressive Illness and X–Chromosome Markers in Three Israeli Pedigrees", Nature Genet. 3:49–55.
Baron et al., 1987, "Genetic Linkage between X–Chromosome Markers and Bipolar Affective Illness", Nature 326:289–292.
Berrettini et al., 1994, "Chromosome 18 DNA Markers and Manic Depressive Illness: Evidence for a Susceptibility Gene", Proc. Natl. Acad. Sci. USA 91:5918–5921.
Bertelson et al., 1977, "A Danish Twin Study of Manic–Depressive Disorders", Br. J. Psychiat. 130:330–351.
Black and Dolnick, 1996, "Expression of rTS Correlates with Altered Growth Regulation of Thymidylate Synthase", Cancer Res. 56:700–705.
Cohen et al., 1993, "Première Génération de la Carte Physique du Génome Humain (A First Generation Physical Map of the Human Genome)", C.R. Acad. Sci. 316:1484–1488 Abstract only.
Cronin et al., 1996, "Cystic Fibrosis Mutation Detection by Hybridization to Light–Generated DNA Probe Arrays", Human Mutation 7:244–255.
Dolnick and Black, 1996, "Alternate Splicing of the rTS Gene Product and Its Overexpression in a 5–Fluorouracil––Resistant Cell Line", Cancer Res. 56:3207–3210.

Dolnick et al., 1993, "Cloning and Characterization of a Naturally Occurring Antisense RNA to Human Thymidylate Synthase mRNA", Nucl. Acids Res. 21:1747–1752.
Egeland et al., 1987, "Bipolar Affective Disorders Linked to DNA Markers on Chromosome 11", Nature 325:783–787.
Freimer et al., 1996, "An Approach to Investigating Linkage for Bipolar Disorder Using Large Costa Rican Pedigrees", Neuropsychiatric Genetics 67:254–263.
Freimer et al., 1996, "Genetic Mapping Using Haplotype, Association and Linkage Methods Suggests a Locus for Severe Bipolar Disorder (BPI) at 18q22–q23", Nature Genetics 12:436–441.
Freimer and Reus, 1992, "The Genetics of Bipolar Disorder and Schizophrenia", in: *The Molecular and Genetic Basis of Neurological Disease*, Rosenberg et al., eds., Butterworths, NY, pp. 951–965.
Houghton et al., 1991, "Generation and Use of Synthetic Peptide Combinatorial Libraries for Basic Resaearch and Drug Discovery", Nature 354:84–86.
Kelsoe et al., 1989, "Re–Evaluation of the Linkage Relationship between Chromosome 11p Loci and the Gene for Bipolar Affective Disorder in the Old Amish", Nature 342:238–243.
Lam et al., 1991, "A New Type of Synthetic Peptide Library for Identifying Ligand–Binding Activity", Nature 354:82–84.
Levinson and Levitt, 1987, "Schizoaffective Mania Reconsidered", Am. J. Psychiatry 144:415–426.
Maier et al., 1995, "Linkage Analysis between Pericentromeric Markers on Chromosome 18 and Bipolar Disorder: A Replication Test", Psychiatry Res. 59:7–15.
McInnes and Freimer, 1995, "Mapping Genes for Psychiatric Disorders and Behavioral Traits", Curr. Opin. Genet. Devel. 5:376–381.
Murray et al., 1994, "A Comprehensive Human Linkage Map with Centimorgan Density", Science 265:2049–2054.
Pauls et al., 1995, "Linkage Analyses of Chromosome 18 Markers Do Not Identify a Major Susceptibility Locus for Bipolar Affective Disorder in the Old Order Amish", Am. J. Hum. Genet. 57:636–643.

(List continued on next page.)

*Primary Examiner*—Eggerton A. Campbell
(74) *Attorney, Agent, or Firm*—Pennie & Edmonds, LLP

(57) ABSTRACT

The present invention relates to the mammalian Hcen-2 gene. The invention relates to methods for the identification of compounds that modulate the expression of Hcen-2 and to using such compounds as therapeutic agents in the treatment of Hcen-2 disorders. The invention also relates to methods for the diagnostic evaluation, genetic testing and prognosis of Hcen-2 mediated disorders, and to methods and compositions for the treatment these disorders. The invention also relates to use of the Hcen-2 gene and/or gene products as markers for fine structure mapping of a region of human chromosome 18, including a region of the chromosome involved in mediating neuropsychiatric disorders.

6 Claims, 4 Drawing Sheets

OTHER PUBLICATIONS

Pauls et al., 1992, "Risks of Affective Illness Among First–Degree Relatives of Bipolar 1 Old–Order Amish Probands", Arch. Gen. Psychiatry 49:703–708.

Rosenthal et al., 1980, "Toward the Validation of RDC Schizoaffective Disorder", Arch. Gen. Psychiatry 37:804–810.

Songyang et al., 1993, "SH2 Domains Recognize Specific Phosphopeptide Sequences", Cell 72:767–778.

Straub et al., 1994, "A Possible Vulnerability Locus for Bipolar Affective Disorder on Chromosome 21q22.3", Nature Genetics 8:291–296.

R. Errabolu, et al., Cloning of a cDNA encoding human centrin, an EF–hand protein of centrosomes and mitotic spindle poles,: *J. Cell Science* (1994), 107:9–16.

```
                                                              M   A   S   G   F   K   K       7
GAATTCGGGGGGCGGTGCCGTTGGGACCACGGCGGCCAGAGCGGCAGG ATG GCT TCC GGC TTC AAG AAG      69

P   S   A   A   S   T   G   Q   K   R   K   V   A   P   K   P   E   L   T   E    27
CCC AGC GCT GCC TCC ACC GGC CAA AAG AGA AAG GTG GCA CCT AAG CCC GAG CTC ACT GAG   129

D   Q   K   Q   E   V   R   E   A   A   F   D   L   F   D   V   D   G   S   G    47
GAT CAG AAG CAA GAA GTT CGG GAA GCA GCA TTT GAC CTC TTC GAC GTG GAC GGA AGT GGG ACC   189

I   D   A   K   E   L   K   V   A   M   R   A   L   G   F   E   P   R   K   E    67
ATC GAC GCG AAG GAG CTG AAG GTG GCC ATG AGA GCG CTG GGC TTC GAA CCC AGG AAG GAA   249

E   M   K   K   M   I   S   E   V   D   R   E   G   T   G   K   I   S   F   N    87
GAG ATG AAG AAA ATG ATC TCC GAG GTG GAC AGG GAA GGC ACG GGG AAG ATC AGC TTC AAT   309

D   F   L   A   V   M   T   Q   K   M   S   E   K   D   T   K   E   E   I   L   107
GAC TTC CTG GCC GTG ATG ACG CAG AAG ATG TCC GAG AAG GAC ACC AAA GAA GAA ATC CTG   369

K   A   F   R   L   F   D   D   D   E   T   G   K   I   S   F   K   N   L   K   127
AAG GCC TTC AGG CTC TTT GAT GAC GAT GAG GAG ACC GGG AAG ATC TCG TTC AAA AAC CTG AAG   429

R   V   A   N   E   L   G   E   N   L   T   D   E   E   L   Q   E   M   I   D   147
CGT GTG GCC AAC GAG CTG GGG GAG AAC CTC ACG GAT GAG GAG CTG CAG GAG ATG ATC GAC   489

E   A   D   R   D   G   D   G   E   V   N   E   E   E   F   L   R   I   M   K   167
GAA GCT GAT CGG GAT GGG GAC GGC GAA GTG AAC GAG GAG GAG TTC CTT CGG ATC ATG AAG   549

K   T   S   L   Y   *                                                             173
AAG ACC AGC CTT TAC TGA                                                            567

AGTCGGTTCAGAAGCTAAAGTGACTCTCTGGGTTGCCTGCTTCCATTTGTGAAACCTTAGAGGACAGGCGGCTGCCTGT   646
CCCTTCTTCACCCCCTCACCCATAATTGTCTAGATCTATTCCATATCTCTAGTTCAATAATAGAATTTGAAAGAT     725
GCTTGTAATGTGAGTTTTTGGGTTTAATTCTCAAGAGCCAACCTGGAGCACATGAGGTTAAACAAAGGGCCTGAAGTT   804
TGAGTGCGCCCTCCATTTGCCTGCTGTCACTTCGTGAACTTGCTGTCATCGTGTTCATCGTGTTCTTGAGGCAGGAGACAGCTTCTGGGACACA   883
CAAAAATGTGGTTCCCTTTGTCACTTCTTGGTGGTCTTAAATATCTTGCTTCATATATCATTCCTTAAATTCCAGTC   962
ATTGTTCCAGCATAATGAGATCTGCCAGTAGATTTGCCTAGCCTGTCCACTTAGCTGAATACCAGTTTGAAGGA     1041
AAACAGGTGGCCACTTACAAACTTACGGAGCTCAGGACAGATATTCTTATAAAGAATAGACTTGCTTGGGTGGTAGTA 1120
CGTTGTGCAATTTGACTATTCACTGGCTTTATACCTGCAAATGCCGAATTC                              1173
```

FIG.1

```
centr-gen
AAGCTTCAGCAGGCCAGGATTTAAATCCCAGAGCCACCATTTATTGGCCATGTACCATTAAATATGTGTTACAGGCCTCTCCTGGGCCT
CATTTTTCATCTGCAAAATAGGAAATGATGGCAAGGATCAAATAAGATGACAACTATGAGAAGCACGCCAAAGCTAGGCACACATT
AAATGTGTTCCCTTCCCTTCTTAAGTCAGAGTTTGGACTCTGAACTATGTACTCCACCAAGAGCTGACTGTGACTATGGCACTG
TTTCTATGAAGGGAGCTCTTGGTGGCCCTTTGTTGTAACTGTTGATTGCACACTTTGCACACATGCACTTTTCCAACACATCATAGCTTGGCTTGAATTTGGGCAGAA
AGCTTGGCCCAAATGTAGCTCTATATAAGGCAGCTTCCATATCCAGTTTTCCAACACATCATAGCTTGGCTTGAATTTGGGCAGAA
GGGTGGGTGCCAAAGGAAATGTACAATGTCTGAGAAAAATTCTTATTCAACTAACAATTACCCAGATCTGTATGGCCCACTAGGCACT
GTCCTGGAGCTTTGTGTAGACTCCCCACTGAAAATGCAGTGGGAAGCTTTATGATGATGAAGATCCCAGGCTTCTGACATGGAAAAGCAGG
GGTGGTTAAGTGACTTTCCAAAGTCACAGAGAATAATAAGGCATAAGACTTGGGATAAGATCCCAGGCTTCTGACATGGAAAAGCAGG
TCACAAGGATTTGCGGTGTTAGAAGAACAGCAGCTGTAGCGTCTGCCTGCCAGTGTGCCTTGAGTTGACACTGTCCACAACAAGTACTG
GAAGGCAGGAGAGGAGGTCCTATGTAAGTTTCCTTGGCCTTTAGAAGAAACCCTGTGTCCAGGCTCTCTGTCAACTAAGTCACATAT
CGAACTGGGGCAGGTAGTGATATATGGCTAATTAAAATGTGCCATGTAACACATATCGACCACTAATTTAAAAACAGTTTGTAAAAC
ATTCCTGGCATCATTAATCTTTGGGGTTTTCGCTTGTGTTGTATCCAGCACTGTGTTTGTTGTTGTTGTTTTGGGACAGAATCTCACTC
AACGAATATATTATTAACCTACTGTGTCACAGGGGCACACAATATCTGCTCACTGCAACATCTGCTAGTCAAGCGATTCCGTGCCTCATATCC
TGTTGCCTAGGGTGGAGTGCAGGGGCACAGTTGTGCGCAGCAACCTGTGCGCAGCAACATCTGCTAGTCAAGCGATTCCGTGCCTCATATCC
CAAGTAGCTGGGATTACAGTTGTGCGCAGCAACCTGCTAGTCCAGCCTAATTTCGTATTTTCATAGAGACAGGGTTTCACCTTGTTGGCCAGG
CTGGTCTTGAACCTCCTGACCTCAGGTGATCCTCCCGGCCTTGGCCTCCCAAATTACTGGGATTACAGGTGTGACCCACTGCGCCCAGCCA
TAAAACTCTTTAACACAAACTCTTCAAAGTGACATCTTGTAACCTTCATAGGTACAAAGGTATTGATATATTAACAGATTGAGAT
TGATTGCGGGGGCGGGGCAGGGGAGAATGCTAAAAAATAAGTCAGCTTTCTTTCTGTAACTATTTAAAAGAATGCAAAGTAAT
TCTACAGGCAATTCCTTGGTGGGCTTATTTGAGTCCCAACATGTCCTGCATCATCTCCTGTGCCCATTGCCAAAGGAAGGCGACCAGAGCGTGGGTTT
TATTCCCAGGAGGCAATTTGAGTCCCAACATGTCCTGCATCATCTCCTGTGCCCATTGCCAAAGGAAGGCGACCAGAGCGTGGGTTT
CAGCACAGCTCGATTGGATGATAAGCAAGGAGAGTAATAATGCTGCTAGGAGGTTAGAGAAAATACTAGAATACTGCAATTATCAAGTGCAATTACCAGAATG
TAGTGTTCCACTTCAAAGCCTCAAATCAAAAGCCTCAAATCAAAAGGCTTGGATATATACACATTGAATTGAAGTGCAATTATCAAGTGCAATTACCAGAATG
ATGGAAACACTGAAAGTAAATCATACATTGGATATTACATAAATTTTCCATTTTCTCTGTTTCCCATTTATGTCAAGTTGAACACATGGTATGA
TGTCAGGAGACAAACTTCTACGCATTTTTATACATAAATTTTCCATTTTCTCTGTTTCCCATTTATGTCAAGTTGAACACATGGTATGA
CTTTAATATTCTCTCTCCTTCCTTCCCACATTGAATGTCAAGTGATCACACTCAATCTTGATTATCCTAAATTTACCCTTAGGA
CCTCTCACCCCATTGGGTGTTGCCGCCAGAAGTAAATCATACATTGGATATTACCATTGAATGTCAAGTGATCACACTCAATCTTGATTATCCTAAATTTACCCTTAGGA
TAATTCTAGCACTTTGGGAGGCTGGGGCGGGAAATCCCTGATCCTGGGTGGTGGTGGCACCAGTGCTGAGGCATGCCCTGTAGTCTCAGCTACTATGGAGGCTGAGGTGGGAGG
CTATAAAAAAAAAAAATTTTTTTAATTTAGCTGGGTGGTGGTGGCACCAGTGCTGAGGCATGCCCTGTAGTCTCAGCTACTATGGAGGCTGAGGTGGGAGG
ATCACTTGATCCTGGAAGGTGGAGGCTGCAGTAAGCTGAGATCGAGCCACTGCACTCCAGCCTGGCCAACATGAGTGAAACCCTGTCTCAAAAGAGAGAGAACTGCCAGCGCCAGTGG
AAAGAGGAAGAGTCCCTAAAGAAAACCTATAAAACTGGGGTCTTATGGATGCGTCAACTCGTGTGAAACCGTTAATGACCCGAGGGACAGCGG
ATTACAGAAGACAACTGTGGCTACAGGCGTCTTGCCAGTCAGGCTGTTCTTGCCAGTCAGGCGATGGGACTAGGAAGAGAGGTTCCCCCGGGCCGGCTCCAGCCCAGGCCCTCCAGCGGGGCGTGGGCGTTGG
ATTCTCGCCTAAGCAAGATCCCGCAGATGGGAAGAGAGGTTCCCCCGGGCCGGCTCCAGCCCAGGCCCTCCAGCGGGGCGTGGGCGTTGG
```

FIG.2A

```
CAGTGAGCGAGGGGTGGTCCCGCGCCGGCGGGGGCGCGCCGAATGAGAGCGCGGGGCGGTGCCGTTGGGACCACGGCCAGA
GCGGCAGGATGGCTTCCGGCTTCAAGAAGCCCAGCGCTGCCTCCACCGGCCAAAAGAGAAAGGTGGCACTAAGCCGAGTCACTGAG
GATCAGAAGCAAGAAGTTCGGAAGCATTTGACCTCTTGACGTGGACGGAAGTGGGACCATCGACGCGAAGGAGCTGAAGGTGGCCAT
GAGAGCGCTGGGCTTCGAACCCAGGAAGAGATGTCCGAGGAAGAAATCCTGAGGTGGACAGGGAAGGCACGGGAAGGATCAGCTTCA
ATGACTTCCTGGCCGTGATGACGCAGAAGATGTCCGAGAAGGACACCAAGAAGAAGAAATCCTGAAGGCCTTCAGGCTCTTTGATGACGAT
GAGACCGGGAAGATCTCGTTCAAAAACCTGAAGCGTGTGGCCAACGAGCTGGGGGAGAACCTCACGGATGAGGAGCTGCAGGAGATGAT
CGACGAAGCTGATCGGGATGGGACGGGAAGTGAACGGCGAAGTGAAGGAGGAGTTCCTTGGATCATGAAGAAGACCAGCCTTACTGAAGTCGGT
TCAGAAGCTAAAGTGACTCTCTGGGTTGCCTGCTTCCATTTGTGAAACCTTGTGAAGATTTCAATATAGAATTTGAAAGATGTTGTAATGTGAGTTTGGGCTC
ACCCCCATAATTTGTCTAGATCTATTCCATATCTCTAGTTCAATATAGAATTTGAAAGATGTTGTAATGTGAGTTTTA
TTCTCAAGAGTCAACCTGAGCACATGAGGTTAAACAAGGCCCTGAAGTTTGAGTGCGCCCTCCATTTGCCCTGTGCTGAACTTGCT
GTTCATCTGTTGATCGGAGGCAGGACAGCTTCTGGGACACACAAAAATGTGGTTCCCTTGTCACTTCTTTGGTGGTCTTAAATTATC
TTGCTTCATATATCATTCTTAAATTCCTAAAGAATTCCAGTCATTGTTCCAGATCTGCCAGTAGATCTATAAAGAATAGACTTGCT
AGTGAATACCAGTTTGAAGGAAAACAGGGTGGCCACTTACACTGGCTTACTGGCTTATTCACTGCTTATAATCTTATACCTGCAAATGATTCTTCGTCATGTGTAAATTGTCCACCATGG
TGGGTGGTAGTACGTTGTGCAATTTGACTATTCACTGCTTATTCACTGGCTACAGAATAAAATCTAATACTGGCCCAAGCAAAGTATAATTGCTTAAGAGG
GTTATCTAGGGCTAGTATGTGAGTATATTTGAGTAATAGCAACAAACATCTTGGTTATTGGACTATTTTACCTCATCTTATTACTGCTTATTATGAG
TTACGCTAACAAACGATTTCCTTGGAAATAGCAACAAACATCTTGGTTATTGGACTATTTTACCTCATCTTATTACTGCTTGATTATGAG
AGCTACTTATAGTCCTGCTAATCTTAGAACATCTTAGAACATCCCCTCTGACATATAGTTGATGTTGATGTCAGAGTGTCTGG
ACACTCTCCCTGCTAATCTTAGAACATCTTGGTTCTTGACTTTGACTCTTCCACTGTGGCTTGTTATGTGGCTTGTTATGTTAATACTGCTTGTTTCTGTTATAA
CATTTCAGTAGTGTCTATTTTACAAATCCCAGTAACTGCTCCAGTACAAATCTGAAGTTAAAGAAAATTTAAAAATGTAATTGTGGGAA
ATTATTTTTGCTTTGGAGTAAGATCTGCTGAGATGGAGGCTTTGACTAATGTTTTAATAACAGGCAACAAACAAAGAGGCAGGATATTTGGTCACAA
AATAACAAATAGATCTGCTGAGATGGAGGCTTTGACTAATGTTTTAATAACAGGCAACAAACAAAGAGGCAGGATATTTGGTCACAA
CTAAACCTAAATTAAATCCTCATACAAAGCCCATTAAGATAAAATGCTCAAATTCTGGGAACATTTCACTTGCTTGCCAGCAATTTTA
CCCTTCAGAGGGTGTGAATCTAATCAGGGGAACAAACTACCCTGGGCTTAATTCTCATTAACAGGGACTAATTTGTCAAAGCGGCAGTA
CTAGCTGAAGTGATGGGTATGGGAAGCATTCACTGTGAGGATTTTGCTGAGGTGCCTGGCACAGGGGTAGGGAACTCACCCAGGCTGCAA
GATGCTAACAGTTCAGGTTCAGGGCAGGCAGTTCAAGTTCAGGGGCAGGTCAAGAGGAACCAGGGAAGAAGTTGGCAGAACAGGTGCAACTTGGCAAGCAGAGTGTCCTGGTATCCTGGTATCGAGTATGA
AGGGCCTGATCTGAGGGCAGGGAGGCAGGGAGGGGCAGGAGTAGAAATAACCAGAAATACCAGAAACCAGGAAGAAACCAGGCTCAACTTGGCAAGAGTCGTCTTGACCAGAGTCTCAGCCAACTGGACTGGGCT
TCAACGTATGAATTAAAGTGCCGGCCTACTGCTGGCCTGGCCTGAAGCCCAGTGCTGAGATAGAAGATAACCAGGAACCCAGGCTGAAGCCTGAAGCCTGAACTGGACTGGGCT
CAGCCTTTGGCTACTGGCCTGGCCTGAAGCCCAGTGCTTGGGCTGGTTGGGCTGGCCACACCATGC
```

FIG.2B

```
ATAGCCTTAAAGGGGTGGCCTAAGGGCATGGTCCGCTCCAAAAAAGGAAAGGGGGCCCCAGAATATTTCTGAATCCCACTCACTGCCAG
GGAAGAACCTCTCAATTCACTCAATAGTGCATTCTCCTGCTTCTCAATAGGCTAATACTCTAGAGAATATGGGGACAAGGGAGGAGGG
TCTAGTGGAACAGGTCTAAACTGGCGTTTGAATTTAAGATAAGTAATCATACATTGGCTGGGTCAGCCATGTCTCTTAGTCTTTACA
AAGTAGAACACAAAAAATTCAATGGAAATCTACAGACACCTATTTGCAGATGAGGAAACACGGCTATGAAGATTGGGAAGATTGGGA
AGAACTGGCCAGGTGTGGTGCTCACGCCTGTAATCCCAGCACTTTGGGAGGCCGAGGCTGGTGGATCACTTGAGGTCAGGAGTTGGAGA
CCAGCCTGGGCAACATAGTAAAACCCTGTCTCTACTCAAATTACAAAAAATTCAGCAGGCGTTGTGGCCCACCTGTAATCCCAGCTAT
GCAGGAGGCTGAGGCAGGACAATCACTTGAACCTGGTAGGCGGAGGTTGCAGTGAGCCAAAATCACGCCACTGTACTCCAGCCTGGGTG
ACAGAGCAAGACTTTGTTTAAAAAAAAAGGGAAGAACTAAAATGTAATTTCAAGGGCTATCACAAATGGTCCCAATAA
AGAGAAAGCAGGACTCATGTTTAAGAAGACCATGAGATGTGTATGGACCTGTCTTGCTTTCTAATGATCTACGTAACAG
ATGAAAAAGCAGGAGCATAGGGCTAAGGATGAAGATGAAAATACAACAGTAATAAGGTATTAATATATTAAGAAAAGCTAATGCTCCACATAAGC
AGAGGACATTAAAGGGACTTTTTTCTTAAGGATATCTTGAGTCTGAGCACTCTGAGTCTGAGAAAATTAATTTGATATGCAGAAAATTAATTTGAATGTGCTTTCAGATCACCCAG
TTGTTGCAGGTTGGTTTCCATCGGAAGCACTCTGAGTCTGAGCACTCTGAGAGAGGCTGGGCTGTAACCAAGTCACACAAAGGTGTCAGCTGGTCCCATGGTGAAT
GTGGGGAGGAGGAGAAACCAGGACTGGGCAGGAGAGAGGCTGGGCTGTAACCAAGTCACACAAAGGTGTCAGCTGGTCCCATGGTGAAT
TCTGGACCTAGGATGGCTGATCCCAAGGCATTCCAAACTGGGCAAGGAAGTTGTGCTTAAAACTTCTCATTGACTGTCAGTCACTGG
GCATGAGCAGTCCCCAGGAAGGGGGATGACCTTGAGCCAAGGTGGATGTCTTCAGCCAAGGGCAATCACTGGGAAGGAGAACCCAGCTA
TGAACTGTCAGCTGCCAACACTCCCAGCATCTGA
```

FIG.2C

METHODS AND COMPOSITIONS FOR THE DIAGNOSIS AND TREATMENT OF NEUROPSYCHIATRIC DISORDERS

CROSS REFERENCE TO RELATED APPLICATIONS

This application is a continuation of prior provisional Application No. 60/080,841, filed Apr. 6, 1998, the entire contents of which are incorporated herein.

1. INTRODUCTION

The present invention relates to drug screening assays, and diagnostic and therapeutic methods for the treatment of neuropsychiatric disorders, mediated by the expression of the mutant form of the human centrin (Hcen-2) gene or by aberrant levels of Hcen-2 expression. The invention is based on Applicant's discovery that the Hcen-2 gene is linked to the short arm of chromosome 18 in a region of the chromosome involved in mediating neuropsychiatric disorders such as bipolar-affected disorder (BAD). Thus, the invention relates to use of the Hcen-2 gene and/or gene products as markers for fine structure mapping of a region of human chromosome 18, including a region of the chromosome involved in mediating neuropsychiatric disorders. The invention also relates to methods for the identification of compounds that modulate the expression, synthesis and activity of the Hcen-2 protein/gene and to using compounds such as those identified as therapeutic agents in the treatment of an Hcen-2 mediated disorder; a neuropsychiatric disorder, including, by way of example and not of limitation, bipolar affective disorder. The invention also relates to methods for the diagnostic evaluation, genetic testing and prognosis of Hcen-2 mediated disorders.

2. BACKGROUND OF THE INVENTION

There are only a few psychiatric disorders in which clinical manifestations of the disorder can be correlated with demonstrable defects in the structure and/or function of the nervous system. Well-known examples of such disorders include Huntington's disease, which can be traced to a mutation in a single gene and in which neurons in the striatum degenerate, and Parkinson's disease, in which dopaminergic neurons in the nigro-striatal pathway degenerate. The vast majority of psychiatric disorders, however, presumably involve subtle and/or undetectable changes, at the cellular and/or molecular levels, in nervous system structure and function. This lack of detectable neurological defects distinguishes "neuropsychiatric" disorders, such as schizophrenia, attention deficit disorders, schizoaffective disorder, bipolar affective disorders, or unipolar affective disorder, from neurological disorders, in which anatomical or biochemical pathologies are manifest. Hence, identification of the causative defects and the neuropathologies of neuropsychiatric disorders are needed in order to enable clinicians to evaluate and prescribe appropriate courses of treatment to cure or ameliorate the symptoms of these disorders.

One of the most prevalent and potentially devastating of neuropsychiatric disorders is bipolar affective disorder (BAD), also known as bipolar mood disorder (BP) or manic-depressive illness, which is characterized by episodes of elevated mood (mania) and depression (Goodwin, et al., 1990, *Manic Depressive Illness,* Oxford University Press, New York). The most severe and clinically distinctive forms of BAD are BP-I (severe bipolar affective (mood) disorder), which affects 2–3 million people in the United States, and SAD-M (schizoaffective disorder manic type). They are characterized by at least one full episode of mania, with or without episodes of major depression (defined by lowered mood, or depression, with associated disturbances in rhythmic behaviors such as sleeping, eating, and sexual activity). BP-I often co-segregates in families with more etiologically heterogeneous syndromes, such as with a unipolar affective disorder such as unipolar major depressive disorder (MDD), which is a more broadly defined phenotype (Freimer and Reus, 1992, in *The Molecular and Genetic Basis of Neurological Disease,* Rosenberg, et al., eds., Butterworths, New York, pp. 951–965; McInnes and Freimer, 1995, Curr. Opin. Genet. Develop., 5, 376–381). BP-I and SAD-M are severe mood disorders that are frequently difficult to distinguish from one another on a cross-sectional basis, follow similar clinical courses, and segregate together in family studies (Rosenthal, et al., 1980, Arch. General Psychiat. 37, 804–810; Levinson and Levitt, 1987, Am. J. Psychiat. 144, 415–426; Goodwin, et al., 1990, *Manic Depressive Illness,* Oxford University Press, New York). Hence, methods for distinguishing neuropsychiatric disorders such as these are needed in order to effectively diagnose and treat afflicted individuals.

Currently, individuals are typically evaluated for BAD using the criteria set forth in the most current version of the American Psychiatric Association's Diagnostic and Statistical Manual of Mental Disorders (DSM). While many drugs have been used to treat individuals diagnosed with BAD, including lithium salts, carbamazepine and valproic acid, none of the currently available drugs are adequate. For example, drug treatments are effective in only approximately 60–70% of individuals diagnosed with BP-I. Moreover, it is currently impossible to predict which drug treatments will be effective in, for example, particular BP-I affected individuals. Commonly, upon diagnosis, affected individuals are prescribed one drug after another until one is found to be effective. Early prescription of an effective drug treatment, therefore, is critical for several reasons, including the avoidance of extremely dangerous manic episodes and the risk of progressive deterioration if effective treatments are not found.

The existence of a genetic component for BAD is strongly supported by segregation analyses and twin studies (Bertelson, et al., 1977, Br. J. Psychiat. 130, 330–351; Freimer and Reus, 1992, in *The Molecular and Genetic Basis of Neurological Disease,* Rosenberg, et al., eds., Butterworths, New York, pp. 951–965; Pauls, et al., 1992, Arch. Gen. Psychiat. 49, 703–708). Efforts to identify the chromosomal location of genes that might be involved in BP-I, however, have yielded disappointing results in that reports of linkage between BP-I and markers on chromosomes X and 11 could not be independently replicated nor confirmed in the re-analyses of the original pedigrees, indicating that with BAD linkage studies, even extremely high lod scores at a single locus, can be false positives (Baron, et al., 1987, Nature 326, 289–292; Egeland, et al., 1987, Nature 325, 783–787; Kelsoe, et al., 1989, Nature 342, 238–243; Baron, et al., 1993, Nature Genet. 3, 49–55).

Recent investigations have suggested possible localization of BAD genes on chromosomes 18p and 21q, but in both cases the proposed candidate region is not well defined and no unequivocal support exists for either location (Berrettini, et al., 1994, Proc. Natl. Acad. Sci. USA 91, 5918–5921; Murray, et al., 1994, Science 265, 2049–2054; Pauls, et al., 1995, Am. J. Hum. Genet. 57, 636–643; Maier,, et al., 1995, Psych. Res. 59, 7–15; Straub, et al., 1994, Nature Genet. 8, 291–296).

Mapping genes for common diseases believed to be caused by multiple genes, such as BAD, may be complicated by the typically imprecise definition of phenotypes, by etiologic heterogeneity, and by uncertainty about the mode of genetic transmission of the disease trait. With neuropsychiatric disorders there is even greater ambiguity in distinguishing individuals who likely carry an affected genotype from those who are genetically unaffected. For example, one can define an affected phenotype for BAD by including one or more of the broad grouping of diagnostic classifications that constitute the mood disorders: BP-I, SAD-M, MDD, and bipolar affective (mood) disorder with hypomania and major depression (BP-II).

Thus, one of the greatest difficulties facing psychiatric geneticists is uncertainty regarding the validity of phenotype designations, since clinical diagnoses are based solely on clinical observation and subjective reports. Also, with complex traits such as neuropsychiatric disorders, it is difficult to genetically map the trait-causing genes because: (1) neuropsychiatric disorder phenotypes do not exhibit classic Mendelian recessive or dominant inheritance patterns attributable to a single genetic locus, (2) there may be incomplete penetrance, i.e., individuals who inherit a predisposing allele may not manifest disease; (3) a phenocopy phenomenon may occur, i.e., individuals who do not inherit a. predisposing allele may nevertheless develop disease due to environmental or random causes; (4) genetic heterogeneity may exist, in which case mutations in any one of several genes may result in identical phenotypes.

Despite these difficulties, however, identification of the chromosomal location, sequence and function of genes and gene products responsible for causing neuropsychiatric disorders such as bipolar affective disorders is of great importance for genetic counseling, diagnosis and treatment of individuals in affected families.

3. SUMMARY OF THE INVENTION

It is an object of the present invention to identify genetic bases for neuropsychiatric disorders, provide methods of treating and diagnosing neuropsychiatric disorders, and provide methods for identifying compounds for use as part of therapeutic and/or diagnostic methods.

The invention further relates to methods for the treatment of Hcen-2 mediated neuropsychiatric disorders, wherein such methods comprise administering a compound which modulates the expression of a mammalian Hcen-2 gene and/or the synthesis or activity of a mammalian Hcen-2 gene product so symptoms of the disorder are ameliorated.

The invention further relates to methods for the treatment of mammalian Hcen-2 mediated neuropsychiatric disorders resulting from Hcen-2 gene mutations, wherein such methods comprise supplying the mammal with a nucleic acid molecule encoding an unimpaired Hcen-2 gene product such that an unimpaired Hcen-2 gene product is expressed and symptoms of the disorder are ameliorated.

The invention further relates to methods for the treatment of mammalian Hcen-2 mediated neuropsychiatric disorders resulting from Hcen-2 gene mutations, wherein such methods comprise supplying the mammal with a cell comprising a nucleic acid molecule that encodes an unimpaired Hcen-2 gene product such that the cell expresses the unimpaired Hcen-2 gene product and symptoms of the disorder are ameliorated.

In addition, the present invention is directed to methods that utilize the Hcen-2 gene and/or gene product sequences for the diagnostic evaluation, genetic testing and prognosis of an Hcen-2 mediated disorder. For example, the invention relates to methods for diagnosing Hcen-2 mediated neuropsychiatric disorders, wherein such methods comprise measuring Hcen-2 gene expression in a patient sample, or detecting an Hcen-2 mutation in the genome of the mammal suspected of exhibiting such a disorder.

The invention still further relates to methods for identifying compounds capable of modulating the expression of the mammalian Hcen-2 gene and/or the synthesis or activity of the mammalian Hcen-2 gene products, wherein such methods comprise contacting a compound to a cell that expresses an Hcen-2 gene, measuring the level of Hcen-2 gene expression, gene product expression or gene product activity, and comparing this level to the level of Hcen-2 gene expression, gene product expression or gene product activity produced by the cell in the absence of the compound, such that if the level obtained in the presence of the compound differs from that obtained in its absence, a compound capable of modulating the expression of the mammalian Hcen-2 gene and/or the synthesis or activity of the mammalian Hcen-2 gene products has been identified.

The invention is based, in part, on the genetic and physical mapping of the Hcen-2 gene to a specific portion of human chromosome 18, and specifically to the short arm of human chromosome 18 between the telomere and D18S481, described in the example presented below in Section 6. Thus, the invention also relates to the use of the Hcen-2 gene and/or gene products as markers for fine structure mapping of this region of human chromosome 18.

The term "Hcen-2 mediated disorder" as used herein refers to a disorder involving an aberrant level of Hcen-2 gene expression, gene product synthesis and/or gene product activity relative to levels found in normal, unaffected, unimpaired individuals, levels found in clinically normal individuals, and/or levels found in a population whose level represents a baseline, average Hcen-2 level.

3.1 Definitions

As used herein, the following terms shall have the abbreviations indicated.

BAC, bacterial artificial chromosomes

BAD, bipolar affective disorder(s)

BP, bipolar mood disorder

BP-I, severe bipolar affective (mood) disorder

BP-II, bipolar affective (mood) disorder with hypomania and major depression bp, base pair(s)

EST, expressed sequence tag lod, logarithm of odds

MDD, unipolar major depressive disorder

ROS, reactive oxygen species

RT-PCR, reverse transcriptase PCR

SSCP, single-stranded conformational polymorphism

SAD-M, schizoaffective disorder manic type

STS, short tag sequence

YAC, yeast artificial chromosome

4. BRIEF DESCRIPTION OF THE FIGURES

FIG. 1. Sequence of the human Hcen-2 gene. Amino acid sequences are indicated.

FIG. 2. Genomic Sequence of the the human Hcen-2 gene. Exons are in bold. The 3' and 5' UTR's are underlined and in bold.

5. DETAILED DESCRIPTION OF THE INVENTION

This invention is based on the genetic and physical mapping of the Hcen-2 gene to a specific, narrow portion of chromosome 18, also described in the Example presented below in Section 6.

The invention described in the subsections below encompasses screening methods (e.g., assays) for the identification of compounds which can be used to treat individuals suffering from an Hcen-2 mediated disorder. The invention also encompasses agonists and antagonists of the Hcen-2 gene product, including small molecules, large molecules, and antibodies, as well as nucleotide sequences that can be used to inhibit Hcen-2 gene expression (e.g., antisense and ribozyme molecules), and gene or regulatory sequence replacement constructs designed to enhance Hcen-2 gene expression (e.g., expression constructs that place the Hcen-2 gene under the control of a strong promoter system).

In particular, cellular and non-cellular assays are described that can be used to identify compounds that interact with the Hcen-2 gene product, e.g., modulate the activity of the Hcen-2 and/or bind to the Hcen-2 gene product. Such cell-based assays of the invention utilize cells, cell lines, or engineered cells or cell lines that express the Hcen-2 gene product.

The invention also encompasses the use of cell-based assays or cell-lysate assays (e.g., in vitro transcription or translation assays) to screen for compounds or compositions that modulate Hcen-2 gene expression. To this end, constructs containing a reporter sequence linked to a regulatory element of the Hcen-2 gene can be used in engineered cells, or in cell lysate extracts, to screen for compounds that modulate the expression of the reporter gene product at the level of transcription. For example, such assays could be used to identify compounds that modulate the expression or activity of transcription factors involved in Hcen-2 gene expression, or to test the activity of triple helix polynucleotides. Alternatively, engineered cells or translation extracts can be used to screen for compounds (including antisense and ribozyme constructs) that modulate the translation of Hcen-2 mRNA transcripts, and therefore, affect expression of the Hcen-2 gene product.

The invention also encompasses Hcen-2 gene products, polypeptides (including soluble Hcen-2 polypeptides or peptides) and Hcen-2 fusion proteins for use in non-cell based screening assays, for use in generating antibodies, for diagnostics and therapeutics. Such peptides or polypeptides can be fused to a heterologous protein, e.g., reporter, an Ig Fc region, etc., to yield a fusion protein. Such peptides, polypeptides and fusion proteins can be used in the non-cell based assays for screening compounds that interact with, e.g., modulate the activity of the Hcen-2 gene product and/or bind to the Hcen-2 gene product.

Hcen-2 proteins can be used to treat disorders. Such Hcen-2 gene products include but are not limited to soluble derivatives such as peptides or polypeptides corresponding to one or more domains of the Hcen-2 gene product. Alternatively, antibodies to the Hcen-2 protein or anti-idiotypic antibodies that mimic the Hcen-2 gene product (including Fab fragments), antagonists or agonists can be used to treat neuropsychiatric disorders involving Hcen-2. In yet another approach, nucleotide constructs encoding such Hcen-2 gene products can be used to genetically engineer host cells to express such Hcen-2 gene products in vivo; these genetically engineered cells can function as "bioreactors" in the body delivering a continuous supply of Hcen-2 gene product, Hcen-2 peptides, soluble Hcen-2 polypeptides.

In addition, this invention presents methods for the diagnostic evaluation and prognosis of Hcen-2 mediated disorders. For example, nucleic acid molecules encoding Hcen-2 can be used as diagnostic hybridization probes or as primers for diagnostic PCR analysis for the identification of Hcen-2 gene mutations, allelic variations and regulatory defects in the Hcen-2 gene.

"Gene therapy" approaches for the modulation of Hcen-2 gene expression and/or activity in the treatment of neuropsychiatric disorders are within the scope of the invention. For example, nucleotide constructs encoding functional Hcen-2 gene, mutant Hcen-2 gene, as well as antisense and ribozyme molecules can be used to modulate Hcen-2 gene expression.

The invention also encompasses pharmaceutical formulations and methods for treating neuropsychiatric disorders involving the Hcen-2 gene. The present invention presents methods for selecting an effective drug to administer to an individual having an Hcen-2 medicated disorder. Such methods are based on the detection of genetic polymorphisms in the Hcen-2 gene or variations in Hcen-2 gene expression due to altered methylation, differential spinning, or post-transductional modification of the Hcen-2 gene product which can affect the safety and efficacy of a therapeutic agent.

5.1 The Hcen-2 Gene

With respect to Hcen-2 gene sequences as disclosed in FIG. 1, such sequences can, for example, be obtained readily by utilizing standard sequencing and bacterial artificial chromosome (BAC) technologies in connection with BAC54 (Identification Reference EpHS996, ATCC Accession No. 98363).

For example, sheared libraries can be made from BAC54. Fragments of a convenient size, e.g., in the size range of approximately 1 kb, are cloned into a standard plasmid, and sequenced. Further Hcen-2 sequences can then readily be identified by alignment of the BAC sequences with the Hcen-2 sequences depicted in FIG. 1. Alternatively, BAC subclones containing additional Hcen-2 sequences can be identified by identifying those subclones which hybridize to probes derived from the Hcen-2 sequences depicted in FIG. 1.

With respect to the cloning of allelic variants of the human Hcen-2 gene and homologues from other species (e.g., mouse), the isolated Hcen-2 gene sequences disclosed herein may be labeled and used to screen a cDNA library constructed from mRNA obtained from appropriate cells or tissues (e.g., brain tissues) derived from the organism (e.g., mouse) of interest. The hybridization conditions used should be of a lower stringency when the cDNA library is derived from an organism different from the type of organism from which the labeled sequence was derived.

Alternatively, the labeled fragment may be used to screen a genomic library derived from the organism of interest, again, using appropriately stringent conditions. Low stringency conditions are well known to those of skill in the art, and will vary predictably depending on the specific organisms from which the library and the labeled sequences are derived. For guidance regarding such conditions see, for example, Sambrook, et al., 1989, Molecular Cloning, A Laboratory Manual, Second Edition, Cold Spring Harbor Press, N.Y.; and Ausubel, et al., 1989, Current Protocols in Molecular Biology, Green Publishing Associates and Wiley Interscience, N.Y.

Further, an Hcen-2 gene allelic variant may be isolated from, for example, human nucleic acid, by performing PCR using two degenerate oligonucleotide primer pools designed on the basis of amino acid sequences within the Hcen-2 gene product disclosed herein. The template for the reaction may be cDNA obtained by reverse transcription of mRNA prepared from, for example, human or non-human cell lines or tissue known or suspected to express an Hcen-2 gene allele (such as human leukemia cell lines e.g., K562 BIA, H630 and H630-1, e.g. Dolnick et al., 1996, Cancer Research 56:1207–3260; Dolnick et al., 1993, Nucleic Acids Res., 21:1747–1752; Black et al., 1996, Cancer Res. 56:700–705). Preferably, the allelic variant will be isolated from an individual who has an Hcen-2 mediated disorder.

The PCR product may be subcloned and sequenced to ensure that the amplified sequences represent the sequences of an Hcen-2 gene nucleic acid sequence. The PCR fragment may then be used to isolate a full length cDNA clone by a variety of methods. For example, the amplified fragment may be labeled and used to screen a bacteriophage cDNA library. Alternatively, the labeled fragment may be used to isolate genomic clones via the screening of a genomic library.

PCR technology may also be utilized to isolate full length cDNA sequences. For example, RNA may be isolated, following standard procedures, from an appropriate cellular or tissue source (i.e., one known, or suspected, to express the Hcen-2 gene, such as, for example, brain tissue samples obtained through biopsy or post-mortem). A reverse transcription reaction may be performed on the RNA using an oligonucleotide primer specific for the most 5' end of the amplified fragment for the priming of first strand synthesis. The resulting RNA/DNA hybrid may then be "tailed" with guanines using a standard terminal transferase reaction, the hybrid may be digested with RNAase H, and second strand synthesis may then be primed with a poly-C primer. Thus, cDNA sequences upstream of the amplified fragment may easily be isolated. For a review of cloning strategies that may be used, see e.g., Sambrook et al., 1989, supra.

As mentioned above, the Hcen-2 gene sequences may be used to isolate mutant Hcen-2 gene alleles, preferably from a human subject. Such mutant alleles may be isolated from individuals either known or proposed to have a genotype that contributes to the symptoms of an Hcen-2 mediated disorder. Mutant alleles and mutant allele products may then be utilized in the therapeutic and diagnostic systems described below. Additionally, such Hcen-2 gene sequences can be used to detect Hcen-2 gene regulatory (e.g., promoter) defects which can be associated with an Hcen-2 mediated neuropsychiatric disorder, a disorder.

A cDNA of a mutant allelic variant of the Hcen-2 gene may be isolated, for example, by using PCR, a technique that is well known to those of skill in the art. In this case, the first cDNA strand may be synthesized by hybridizing an oligo-dT oligonucleotide to mRNA isolated from tissue known or suspected to be expressed in an individual putatively carrying the mutant Hcen-2 allele, and by extending the new strand with reverse transcriptase. The second strand of the cDNA is then synthesized using an oligonucleotide that hybridizes specifically to the 5' end of the normal gene. Using these two primers, the product is then amplified via PCR, cloned into a suitable vector, and subjected to DNA sequence analysis through methods well known to those of skill in the art. By comparing the DNA sequence of the mutant Hcen-2 allele to that of the normal Hcen-2 allele, the mutation(s) responsible for the loss or alteration of function of the mutant Hcen-2 gene product can be ascertained.

Alternatively, a genomic library can be constructed using DNA obtained from an individual suspected of or known to carry a mutant Hcen-2 allele, or a cDNA library can be constructed using RNA from a tissue known, or suspected, to express a mutant Hcen-2 allele. An unimpaired Hcen-2 gene or any suitable fragment thereof may then be labeled and used as a probe to identify the corresponding mutant Hcen-2 allele in such libraries. Clones containing the mutant Hcen-2 gene sequences may then be purified and subjected to sequence analysis according to methods well known to those of skill in the art.

Additionally, an expression library can be constructed utilizing cDNA synthesized from, for example, RNA isolated from a tissue known, or suspected, to express a mutant Hcen-2 allele in an individual suspected of or known to carry such a mutant allele. In this manner, gene products made by the putatively mutant tissue may be expressed and screened using standard antibody screening techniques in conjunction with antibodies raised against the normal Hcen-2 gene product, as described, below, in section 5.3. (For screening techniques, see, for example, Harlow and Lane, eds., 1988, "Antibodies: A Laboratory Manual", Cold Spring Harbor Press, Cold Spring Harbor.)

In cases where an Hcen-2 mutation results in an expressed gene product with altered function (e.g., as a result of a missense or a frameshift mutation), a polyclonal set of anti-Hcen-2 gene product antibodies are likely to cross-react with the mutant Hcen-2 gene product. Library clones detected via their reaction with such labeled antibodies can be purified and subjected to sequence analysis according to methods well known to those of skill in the art.

Hcen-2 mutations can further be detected using PCR amplification techniques. Primers can routinely be designed to amplify overlapping regions of the whole Hcen-2 sequence including the promoter region. In one embodiment, primers are designed to cover the exon-intron boundaries such that, coding regions can be scanned for mutations (see, FIG. 2). Several primers for analysing various Hcen-2 exons are provided in the Examples.

Genomic DNA isolated from lymphocytes of normal and affected individuals is used as PCR template. PCR products from normal and affected individuals are compared, either by single strand conformational polymorphism (SSCP) mutation detection techniques and/or by sequencing. The mutations responsible for the loss or alteration of function of the mutant Hcen-2 gene product can then be ascertained.

5.2. Protein Products of the Hcen-2 Gene

Hcen-2 gene products, or peptide fragments thereof, can be prepared for a variety of uses. For example, such gene products, or peptide fragments thereof, can be used for the generation of antibodies, in diagnostic assays, or for the identification of other cellular or extracellular gene products involved in the regulation of Hcen-2 mediated disorders.

The amino acid sequence depicted in FIG. 1 represents an Hcen-2 gene product. The Hcen-2 gene product, sometimes referred to herein as an "Hcen-2 protein", includes those gene products encoded by the Hcen-2 gene sequences depicted in FIG. 1, as well as other human allelic variants of Hcen-2 that can be identified by the methods herein described.

In addition, Hcen-2 gene products may include proteins that represent functionally equivalent gene products. Such an equivalent Hcen-2 gene product may contain deletions, including internal deletions, additions, including additions yielding fusion proteins, or substitutions of amino acid residues within and/or adjacent to the amino acid sequence encoded by the Hcen-2 gene sequences described, above, in Section 5.1, but that result in a "silent" change, in that the change produces a functionally equivalent Hcen-2 gene product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

Alternatively, where alteration of function is desired, deletion or non-conservative alterations can be engineered to produce altered, including reduced Hcen-2 gene products. Such alterations can, for example, alter one or more of the biological functions of the Hcen-2 gene product. Further, such alterations can be selected so as to generate Hcen-2 gene products that are better suited for expression, scale up, etc. in the host cells chosen. For example, cysteine residues can be deleted or substituted with another amino acid residue in order to eliminate disulfide bridges.

The Hcen-2 gene products, peptide fragments thereof and fusion proteins thereof, may be produced by recombinant DNA technology using techniques well known in the art. Thus, methods for preparing the Hcen-2 gene products, polypeptides, peptides, fusion peptide and fusion polypeptides of the invention by expressing nucleic acid containing Hcen-2 gene sequences are described herein. Methods that are well known to those skilled in the art can be used to construct expression vectors containing Hcen-2 gene product coding sequences and appropriate transcriptional and translational control signals. These methods include, for example, in vitro recombinant DNA techniques, synthetic techniques, and in vivo genetic recombination. See, for example, the techniques described in Sambrook, et al., 1989, supra, and Ausubel, et al., 1989, supra. Alternatively, RNA capable of encoding Hcen-2 gene product sequences may be chemically synthesized using, for example, synthesizers. See, for example, the techniques described in "Oligonucleotide Synthesis", 1984, Gait, ed., IRL Press, Oxford.

A variety of host-expression vector systems may be utilized to express the Hcen-2 gene product coding sequences of the invention. Such host-expression systems represent vehicles by which the coding sequences of interest may be produced and subsequently purified, but also represent cells that may, when transformed or transfected with the appropriate nucleotide coding sequences, exhibit the Hcen-2 gene product of the invention in situ. These include but are not limited to microorganisms such as bacteria (e.g., *E. coli, B. subtilis*) transformed with recombinant bacteriophage DNA, plasmid DNA or cosmid DNA expression vectors containing Hcen-2 gene product coding sequences; yeast (e.g., Saccharomyces, Pichia) transformed with recombinant yeast expression vectors containing the Hcen-2 gene product coding sequences; insect cell systems infected with recombinant virus expression vectors (e.g., baculovirus) containing the Hcen-2 gene product coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing Hcen-2 gene product coding sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the Hcen-2 gene product being expressed. For example, when a large quantity of such a protein is to be produced, for the generation of pharmaceutical compositions of Hcen-2 gene product or for raising antibodies to Hcen-2 gene product, for example, vectors that direct the expression of high levels of fusion protein products that are readily purified may be desirable. Such vectors include, but are not limited, to the *E. coli* expression vector pUR278 (Ruther et; al., 1983, EMBO J. 2, 1791), in which the Hcen-2 gene product coding sequence may be ligated individually into the vector in frame with the lac Z coding region so that a fusion protein is produced; pIN vectors (Inouye and Inouye, 1985, Nucleic Acids Res. 13, 3101–3109; Van Heeke and Schuster, 1989, J. Biol. Chem. 264, 5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica*, nuclear polyhedrosis virus (AcNPV) is used as a vector to express foreign genes. The virus grows in *Spodoptera frugiperda* cells. The Hcen-2 gene product coding sequence may be cloned individually into non-essential regions (for example the polyhedrin gene) of the virus and placed under control of an AcNPV promoter (for example the polyhedrin promoter). Successful insertion of Hcen-2 gene product coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (e.g., see Smith, et al., 1983, J. Virol. 46, 584; Smith, U.S. Pat. No. 4,215,051).

In mammalian host cells, a number of viral-based expression systems may be utilized. In cases where an adenovirus is used as an expression vector, the Hcen-2 gene product coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing Hcen-2 gene product in infected hosts. (e.g., See Logan and Shenk, 1984, Proc. Natl. Acad. Sci. USA 81, 3655–3659). Specific initiation signals may also be required for efficient translation of inserted Hcen-2 gene product coding sequences. These signals include the ATG initiation codon and adjacent sequences. In cases where an entire Hcen-2 gene, including its own initiation codon and adjacent sequences, is inserted into the appropriate expression vector, no additional translational control signals may be needed. However, in cases where only a portion of the Hcen-2 gene coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner, et al., 1987, Methods in Enzymol. 153, 516–544).

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, and WI38.

For long-term, high-yield production of recombinant proteins, stable expression is preferred. For example, cell lines that stably express the Hcen-2 gene product may be engineered. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci that in turn can be cloned and expanded into cell lines. This method may advantageously be used to engineer cell lines that express the Hcen-2 gene product. Such engineered cell lines may be particularly useful in screening and evaluation of compounds that affect the endogenous activity of the Hcen-2 gene product.

A number of selection systems may be used, including but not limited to the herpes simplex virus thymidine kinase (Wigler, et al., 1977, Cell 11, 223), hypoxanthine-guanine phosphoribosyltransferase (Szybalska and Szybalski, 1962, Proc. Natl. Acad. Sci. USA 48, 2026), and adenine phosphoribosyltransferase (Lowy, et al., 1980, Cell 22, 817) genes can be employed in tk$^-$, hgprt$^-$ or aprt$^-$ cells, respectively. Also, antimetabolite resistance can be used as the basis of selection for the following genes: dhfr, which confers resistance to methotrexate (Wigler, et al., 1980, Natl. Acad. Sci. USA 77, 3567; O'Hare, et al., 1981, Proc. Natl. Acad. Sci. USA 78, 1527); gpt, which confers resistance to mycophenolic acid (Mulligan and Berg, 1981, Proc. Natl. Acad. Sci. USA 78, 2072); neo, which confers resistance to the aminoglycoside G-418 (Colberre-Garapin, et al., 1981, J. Mol. Biol. 150, 1); and hygro, which confers resistance to hygromycin (Santerre, et al., 1984, Gene 30, 147).

Alternatively, any fusion protein may be readily purified by utilizing an antibody specific for the fusion protein being expressed. For example, a system described by Janknecht, et al. allows for the ready purification of non-denatured fusion proteins expressed in human cell lines (Janknecht, et al., 1991, Proc. Natl. Acad. Sci. USA 88, 8972–8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$·nitriloacetic acid-agarose columns and histidine-tagged proteins are selectively eluted with imidazole-containing buffers.

The Hcen-2 gene products can also be expressed in transgenic animals. Animals of any species, including, but not limited to, mice, rats, rabbits, guinea pigs, pigs, micropigs, goats, sheep, and non-human primates, e.g., baboons, monkeys, and chimpanzees may be used to generate Hcen-2 transgenic animals. The term "transgenic," as used herein, refers to animals expressing Hcen-2 gene sequences from a different species (e.g., mice expressing human Hcen-2 gene sequences), as well as animals that have been genetically engineered to overexpress endogenous (i.e., same species) Hcen-2 sequences or animals that have been genetically engineered to no longer express endogenous Hcen-2 gene sequences (i.e., "knock-out" animals), and their progeny.

Any technique known in the art may be used to introduce an Hcen-2 gene transgene into animals to produce the founder lines of transgenic animals. Such techniques include, but are not limited to pronuclear microinjection (Hoppe and Wagner, 1989, U.S. Pat. No. 4,873,191); retrovirus mediated gene transfer into germ lines (Van der Putten, et al., 1985, Proc. Natl. Acad. Sci., USA 82, 6148–6152); gene targeting in embryonic stem cells (Thompson, et al., 1989, Cell 56, 313–321); electroporation of embryos (Lo, 1983, Mol. Cell. Biol. 3, 1803–1814); and sperm-mediated gene transfer (Lavitrano et al., 1989, Cell 57, 717–723) (For a review of such techniques, see Gordon, 1989, Transgenic Animals, Intl. Rev. Cytol. 115, 171–229).

Any technique known in the art may be used to produce transgenic animal clones containing an Hcen-2 transgene, for example, nuclear transfer into enucleated oocytes of nuclei from cultured embryonic, fetal or adult cells induced to quiescence (Campbell, et al., 1996, Nature 380, 64–66; Wilmut, et al., Nature 385, 810–813).

The present invention provides for transgenic animals; that carry an Hcen-2 transgene in all their cells, as well as animals that carry the transgene in some, but not all their cells, i.e., mosaic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al. (Lasko, et al., 1992, Proc. Natl. Acad. Sci. USA 89, 6232–6236). The regulatory sequences required for such a cell-type specific activation will depend upon the particular cell type of interest, and will be apparent to those of skill in the art. When it is desired that the Hcen-2 transgene be integrated into the chromosomal site of the endogenous Hcen-2 gene, gene targeting is preferred. Briefly, when such a technique is to be utilized, vectors containing some nucleotide sequences homologous to the endogenous Hcen-2 gene are designed for the purpose of integrating, via homologous recombination with chromosomal sequences, into and disrupting the function of the nucleotide sequence of the endogenous Hcen-2 gene. The transgene may also be selectively introduced into a particular cell type, thus inactivating the endogenous Hcen-2 gene in only that cell type, by following, for example, the teaching of Gu, et al. (Gu, et al., 1994, Science 265, 103–106). The regulatory sequences required for such a cell-type specific inactivation will depend upon the particular cell type of interest, and will be apparent to those of skill in the art.

Once transgenic animals have been generated, the expression of the recombinant Hcen-2 gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques that include but are not limited to Northern blot analysis of tissue samples obtained from the animal, in situ hybridization analysis, and RT-PCR (reverse transcriptase PCR). Samples of Hcen-2 gene-expressing tissue, may also be evaluated immunocytochemically using antibodies specific for the Hcen-2 transgene product.

5.3. Antibodies to Hcen-2 Gene Products

Described herein are methods for the production of antibodies capable of specifically recognizing one or more Hcen-2 gene product epitopes or epitopes of conserved variants or peptide fragments of the Hcen-2 gene products. Further, antibodies that specifically recognize mutant forms of Hcen-2, are encompassed by the invention.

Such antibodies may include, but are not limited to, polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above. Such antibodies may be used, for example, in the detection of an Hcen-2 gene product in an biological sample and may, therefore, be utilized as part of a diagnostic or prognostic technique whereby patients may be tested for abnormal levels of Hcen-2 gene products, and/or for the presence of abnormal forms of such gene products. Such antibodies may also be utilized in conjunction with, for example, compound screening schemes, as described, below, in Section 5.8, for the evaluation of the effect of test compounds on Hcen-2 gene product levels and/or activity. Additionally, such antibodies can be used in conjunction with the gene therapy techniques described, below, in Section 5.9.2 to, for example, evaluate the normal and/or engineered Hcen-2 expressing cells prior to their introduction into the patient.

Anti-Hcen-2 gene product antibodies may additionally be used in methods for inhibiting abnormal Hcen-2 gene product activity. Thus, such antibodies may, therefore, be utilized as part of treatment methods for an Hcen-2 mediated disorder.

For the production of antibodies against an Hcen-2 gene product, various host animals may be immunized by injection with an Hcen-2 gene product, or a portion thereof. Such host animals may include, but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Cozynebacterium parvum*.

Polyclonal antibodies are heterogeneous populations of antibody molecules derived from the sera of animals immunized with an antigen, such as an Hcen-2 gene product, or an antigenic functional derivative thereof. For the production of polyclonal antibodies, host animals such as those described above, may be immunized by injection with Hcen-2 gene product supplemented with adjuvants as also described above.

Monoclonal antibodies, which are homogeneous populations of antibodies to a particular antigen, may be obtained by any technique that provides for the production of antibody molecules by continuous cell lines in culture. These include, but are not limited to, the hybridoma technique of Kohler and Milstein, (1975, Nature 256, 495–497; and U.S. Pat. No. 4,376,110), the human B-cell hybridoma technique (Kosbor et al., 1983, Immunology Today 4, 72; Cole et al., 1983, Proc. Natl. Acad. Sci. USA 80, 2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison, et al., 1984, Proc. Natl. Acad. Sci., 81, 6851–6855; Neuberger, et al., 1984, Nature 312, 604–608; Takeda, et al., 1985, Nature, 314, 452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a marine mAb and a human immunoglobulin constant region. (See, e.g., Cabilly et al., U.S. Pat. No. 4,816,567; and Boss et al., U.S. Pat. No. 4,816397, which are incorporated herein by reference in their entirety.)

In addition, techniques have been developed for the production of humanized antibodies. (See, e.g., Queen, U.S. Pat. No. 5,585,089, which is incorporated herein by reference in its entirety.) An immunoglobulin light or heavy chain variable region consists of a "framework" region interrupted by three hypervariable regions, referred to as complementarily determining regions (CDRs). The extent of the framework region and CDRs have been precisely defined (see, "Sequences of Proteins of Immunological Interest", Kabat, E. et al., U.S. Department of Health and Human Services (1983). Briefly, humanized antibodies are antibody molecules from non-human species having one or more CDRs from the non-human species and a framework region from a human immunoglobulin molecule.

Alternatively, techniques described for the production of single chain antibodies (U.S. Pat. 4,946,778; Bird, 1988, Science 242, 423–426; Huston, et al., 1988, Proc. Natl. Acad. Sci. USA 85, 5879–5883; and Ward, et al., 1989, Nature 334, 544–546) can be adapted to produce single chain antibodies against Hcen-2 gene products. Single chain antibodies are formed by linking the heavy and light chain fragments of the Fv region via an amino acid bridge, resulting in a single chain polypeptide.

Antibody fragments that recognize specific epitopes may be generated by known techniques. For example, such fragments include but are not limited to: the F(ab')$_2$ fragments, which can be produced by pepsin digestion of the antibody molecule and the Fab fragments, which can be generated by reducing the disulfide bridges of the F(ab')$_2$ fragments. Alternatively, Fab expression libraries may be constructed (Huse, et al., 1989, Science, 246, 1275–1281) to allow rapid and easy identification of monoclonal Fab fragments with the desired specificity.

5.4. Uses of Hcen-2 Gene Sequences
Gene Products, and Antibodies

Described herein are various applications of Hcen-2 gene sequences, Hcen-2 gene products, including peptide fragments and fusion proteins thereof, and of antibodies directed against Hcen-2 gene products and peptide fragments thereof. Such applications include, for example, prognostic and diagnostic evaluation of an Hcen-2 mediated disorder BAD, and the identification of subjects with a predisposition to such disorders, as described, below, in Section 5.5. Additionally, such applications include methods for the treatment of an Hcen-2 mediated disorder as described, below, in Section 5.9, and for the identification of compounds that modulate the expression of the Hcen-2 gene and/or the synthesis or activity of the Hcen-2 gene product, as described below, in Section 5.8. Such compounds can include, for example, other cellular products that are involved in Hcen-2 mediated disorders. These compounds can be used, for example, in the amelioration of Hcen-2 mediated disorders.

5.5. Diagnosis of Abnormalities of an Hcen-2, Mediated Disorder

A variety of methods can be employed for the diagnostic and prognostic evaluation of Hcen-2 mediated disorders and for the identification of subjects having a predisposition to such disorders.

Such methods may, for example, utilize reagents such as the Hcen-2 gene nucleotide sequences described in Sections 5.1, and antibodies directed against Hcen-2 gene products, including peptide fragments thereof, as described, above, in Section 5.3. Specifically, such reagents may be used, for example, for:

(1) the detection of the presence of Hcen-2 gene mutations, or the detection of either over- or under-expression of Hcen-2 protein;

(2) the detection of over- or under-abundance of Hcen-2 gene product; and (3) the detection of an aberrant level of Hcen-2 gene product activity.

Hcen-2 gene nucleotide sequences can, for example, be used to diagnose an Hcen-2 mediated disorder using, for example, the techniques for Hcen-2 mutation detection described above in Section 5.1.

Mutations at a number of different genetic loci may lead to phenotypes related to Hcen-2 mediated disorders. Ideally, the treatment of patients suffering from such an Hcen-2 mediated disorder will be designed to target the particular genetic loci containing the mutation mediating the disorder. Genetic polymorphisms have been linked to differences in drug effectiveness. Thus, identification of alterations in the Hcen-2 gene or protein can be utilized to optimize therapeutic drug treatments.

In an embodiment of the present invention, polymorphisms in the Hcen-2 gene sequence, or variations in Hcen-2 gene expression due to altered methylation, differential splicing, or post-translational modification of the Hcen-2 gene product, may be utilized to identify an individual having a disease or condition resulting from an Hcen-2 mediated disorder and thus define the most effective and safest drug treatment. Assays such as those described herein may be used to identify such polymorphisms or variations in Hcen-2 gene expression activity. Once a polymorphism in the Hcen-2 gene, or a variation in Hcen-2 gene expression has been identified in an individual, an appropriate drug treatment can be prescribed to the individual.

The methods described herein may be performed, for example, by utilizing pre-packaged diagnostic kits comprising at least one specific Hcen-2 gene nucleic acid or anti-Hcen-2 gene product antibody reagent described herein, which may be conveniently used, e.g., in clinical settings, to diagnose patients exhibiting abnormalities of an Hcen-2 mediated disorder.

For the detection of Hcen-2 gene mutations, any nucleated cell can be used as a starting source for genomic nucleic acid. For the detection of Hcen-2 gene expression or Hcen-2 gene products, any cell type or tissue in which the Hcen-2 gene is expressed may be utilized.

Nucleic acid-based detection techniques are described, below, in Section 5.6. Peptide detection techniques are described, below, in Section 5.7.

5.6. Detection of Hcen-2 Nucleic Acid Molecules

A variety of methods can be employed to screen for the presence of Hcen-2 gene-specific mutations and to detect and/or assay levels of Hcen-2 nucleic acid sequences.

Mutations within the Hcen-2 gene can be detected by utilizing a number of techniques. Nucleic acid from any nucleated cell can be used as the starting point for such assay techniques, and may be isolated according to standard nucleic acid preparation procedures that are well known to those of skill in the art.

Hcen-2 nucleic acid sequences may be used in hybridization or amplification assays of biological samples to detect abnormalities involving Hcen-2 gene structure, including point mutations, insertions, deletions, inversions, translocations and chromosomal rearrangements. Such assays may include, but are not limited to, Southern analyses, single-stranded conformational polymorphism analyses (SSCP), and PCR analyses.

Diagnostic methods for the detection of Hcen-2 gene-specific mutations can involve for example, contacting and incubating nucleic acids including recombinant DNA molecules, cloned genes or degenerate variants thereof, obtained from a sample, e.g., derived from a patient sample or other appropriate cellular source, such as lymphocytes, with one or more labeled nucleic acid reagents including recombinant DNA molecules, cloned genes or degenerate variants thereof, as described in Section 5.1, under conditions favorable for the specific annealing of these reagents to their complementary sequences within the Hcen-2 gene. The diagnostic methods of the present invention further encompass contacting and incubating nucleic acids for the detection of single nucleotide mutations or polymorphisms of the Hcen-2 gene. Preferably, the lengths of these nucleic acid reagents are at least 15 to 30 nucleotides. After incubation, all non-annealed nucleic acids are removed from the nucleic acid: Hcen-2 molecule hybrid. The presence of nucleic acids that have hybridized, if any such molecules exist, is then detected. Using such a detection scheme, the nucleic acid from the cell type or tissue of interest can be immobilized, for example, to a solid support such as a membrane, or a plastic surface such as that on a microtiter plate or polystyrene beads. In this case, after incubation, non-annealed, labeled nucleic acid reagents of the type described in Section 5.1 are easily removed. Detection of the remaining, annealed, labeled Hcen-2 nucleic acid reagents is accomplished using standard techniques well-known to those in the art. The Hcen-2 gene sequences to which the nucleic acid reagents have annealed can be compared to the annealing pattern expected from a normal Hcen-2 gene sequence in order to determine whether an Hcen-2 gene mutation is present.

In a preferred embodiment, Hcen-2 mutations or polymorphisms can be detected by using a microassay of Hcen-2 nucleic acid sequences immobilized to a substrate or "gene chip" (see, e.g. Cronin, et al., 1996, Human Mutation 7:244–255).

Alternative diagnostic methods for the detection of Hcen-2 gene specific nucleic acid molecules, in patient samples or other appropriate cell sources, may involve their amplification, e.g., by PCR (the experimental embodiment set forth in Mullis, 1987, U.S. Pat. No. 4,683,202), followed by the detection of the amplified molecules using techniques well known to those of skill in the art. The resulting amplified sequences can be compared to those that would be expected if the nucleic acid being amplified contained only normal copies of the Hcen-2 gene in order to determine whether an Hcen-2 gene mutation exists.

Additionally, well-known genotyping techniques can be performed to identify individuals carrying Hcen-2 gene mutations. Such techniques include, for example, the use of restriction fragment length polymorphisms (RFLPs), which involve sequence variations in one of the recognition sites for the specific restriction enzyme used.

Additionally, improved methods for analyzing DNA polymorphisms, which can be utilized for the identification of Hcen-2 gene-specific mutations, have been described that capitalize on the presence of variable numbers of short, tandemly repeated DNA sequences between the restriction enzyme sites. For example, Weber (U.S. Pat. No. 5,075,217) describes a DNA marker based on length polymorphisms in blocks of (dC-dA)n-(dG-dT)n short tandem repeats. The average separation of (dC-dA)n-(dG-dT)n blocks is estimated to be 30,000–60,000 bp. Markers that are so closely spaced exhibit a high frequency co-inheritance, and are extremely useful in the identification of genetic mutations, such as, for example, mutations within the Hcen-2 gene, and the diagnosis of diseases and disorders related to Hcen-2 mutations.

Also, Caskey et al. (U.S. Pat. No. 5,364,759) describe a DNA profiling assay for detecting short tri and tetra nucleotide repeat sequences. The process includes extracting the DNA of interest, such as the Hcen-2 gene, amplifying the extracted DNA, and labelling the repeat sequences to form a genotypic map of the individual's DNA.

The level of Hcen-2 gene expression can also be assayed. For example, RNA from a cell type or tissue known, or suspected, to express the Hcen-2 gene, such as brain, may be isolated and tested utilizing hybridization or PCR techniques such as are described, above. The isolated cells can be derived from cell culture or from a patient. The analysis of cells taken from culture may be a necessary step in the assessment of cells to be used as part of a cell-based gene therapy technique or, alternatively, to test the effect of compounds on the expression of the Hcen-2 gene. Such analyses may reveal both quantitative and qualitative aspects of the expression pattern of the Hcen-2 gene, including activation or inactivation of Hcen-2 gene expression.

In one embodiment of such a detection scheme, a cDNA molecule is synthesized from an RNA molecule of interest (e.g., by reverse transcription of the RNA molecule into cDNA). A sequence within the cDNA is then used as the template for a nucleic acid amplification reaction, such as a PCR amplification reaction, or the like. The nucleic acid reagents used as synthesis initiation reagents (e.g., primers) in the reverse transcription and nucleic acid amplification steps of this method are chosen from among the Hcen-2 gene nucleic acid reagents described in Section 5.1. The preferred lengths of such nucleic acid reagents are at least 9–30 nucleotides. For detection of the amplified product, the nucleic acid amplification may be performed using radioactively or non-radioactively labeled nucleotides. Alternatively, enough amplified product may be made such that the product may be visualized by standard ethidium bromide staining or by utilizing any other suitable nucleic acid staining method.

Additionally, it is possible to perform such Hcen-2 gene expression assays "in situ", i.e., directly upon tissue sections (fixed and/or frozen) of patient tissue obtained from biopsies or resections, such that no nucleic acid purification is necessary. Nucleic acid reagents such as those described in Section 5.1 may be used as probes and/or primers for such in situ procedures (see, for example, Nuovo, G. J., 1992, "PCR In Situ Hybridization: Protocols And Applications", Raven Press, N.Y.).

Alternatively, if a sufficient quantity of the appropriate cells can be obtained, standard Northern analysis can be performed to determine the level of mRNA expression of the Hcen-2 gene.

5.7. Detection of Hcen-2 Gene Products

Antibodies directed against unimpaired or mutant Hcen-2 gene products or conserved variants or peptide fragments thereof, which are discussed, above, in Section 5.3, may also be used as diagnostics and prognostics for an Hcen-2 mediated disorder. Such methods may be used to detect abnormalities in the level of Hcen-2 gene product synthesis or expression, or abnormalities in the structure, temporal expression, and/or physical location of Hcen-2 gene product. The antibodies and immunoassay methods described herein have, for example, important in vitro applications in assessing the efficacy of treatments for Hcen-2 mediated disorders. Antibodies, or fragments of antibodies, such as those described below, may be used to screen potentially therapeutic compounds in vitro to determine their effects on Hcen-2 gene expression and Hcen-2 gene product production. The compounds that have beneficial effects on an Hcen-2 mediated disorder.

In vitro immunoassays may also be used, for example, to assess the efficacy of cell-based gene therapy for an Hcen-2 mediated disorder. Antibodies directed against Hcen-2 gene products may be used in vitro to determine, for example, the level of Hcen-2 gene expression achieved in cells genetically engineered to produce Hcen-2 gene product. In the case of intracellular Hcen-2 gene products, such an assessment is done, preferably, using cell lysates or extracts. Such analysis will allow for a determination of the number of transformed cells necessary to achieve therapeutic efficacy in vivo, as well as optimization of the gene replacement protocol.

The tissue or cell type to be analyzed will generally include those that are known, or suspected, to express the Hcen-2 gene. The protein isolation methods employed herein may, for example, be such as those described in Harlow and Lane (1988, "Antibodies: A Laboratory Manual", Cold Spring Harbor Laboratory Press, Cold spring Harbor, N.Y. ). The isolated cells can be derived from cell culture or from a patient. The analysis of cells taken from culture may be a necessary step in the assessment of cells to be used as part of a cell-based gene therapy technique or, alternatively, to test the effect of compounds on the expression of the Hcen-2 gene.

Preferred diagnostic methods for the detection of Hcen-2 gene products, conserved variants or peptide fragments thereof, may involve, for example, immunoassays wherein the Hcen-2 gene products or conserved variants or peptide fragments are detected by their interaction with an anti-Hcen-2 gene product-specific antibody.

For example, antibodies, or fragments of antibodies, such as those described, above, in Section 5.3, may be used to quantitatively or qualitatively detect the presence of Hcen-2 gene products or conserved variants or peptide fragments thereof. This can be accomplished, for example, by immunofluorescence techniques employing a fluorescently labeled antibody (see below, this Section) coupled with light microscopic, flow cytometric, or fluorimetric detection. Such techniques are especially preferred for Hcen-2 gene products that are expressed on the cell surface.

The antibodies (or fragments thereof) useful in the present invention may, additionally, be employed histologically, as in immunofluorescence or immunoelectron microscopy, for in situ detection of Hcen-2 gene products, conserved variants or peptide fragments thereof. In situ detection may be accomplished by removing a histological specimen from a patient, and applying thereto a labeled antibody that binds to an rTs polypeptide. The antibody (or fragment) is preferably applied by overlaying the labeled antibody (or fragment) onto a biological sample. Through the use of such a procedure, it is possible to determine not only the presence of the Hcen-2 gene product, conserved variants or peptide fragments, but also its distribution in the examined tissue. Using the present invention, those of ordinary skill will readily recognize that any of a wide variety of histological methods (such as staining procedures) can be modified in order to achieve in situ detection of an Hcen-2 gene product.

Immunoassays for Hcen-2 gene products, conserved variants, or peptide fragments thereof will typically comprise incubating a sample, such as a biological fluid, a tissue extract, freshly harvested cells, or lysates of cells in the presence of a detectably labeled antibody capable of identifying Hcen-2 gene product, conserved variants or peptide fragments thereof, and detecting the bound antibody by any of a number of techniques well-known in the art.

The biological sample may be brought in contact with and immobilized onto a solid phase support or carrier, such as nitrocellulose, that is capable of immobilizing cells, cell particles or soluble proteins. The support may then be washed with suitable buffers followed by treatment with the detectably labeled Hcen-2 gene product specific antibody. The solid phase support may then be washed with the buffer a second time to remove unbound antibody. The amount of bound label on the solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

One of the ways in which the Hcen-2 gene product-specific antibody can be detectably labeled is by linking the same to an enzyme, such as for use in an enzyme immunoassay (EIA) (Voller, A., "The Enzyme Linked Immunosorbent Assay (ELISA)", 1978, Diagnostic Horizons 2, 1–7, Microbiological Associates Quarterly Publication, Walkersville, Md.); Voller, A. et al., 1978, J. Clin. Pathol. 31, 507–520; Butler, J. E., 1981, Meth. Enzymol. 73, 482–523; Maggio, E. (ed.), 1980, Enzyme Immunoassay, CRC Press, Boca Raton, Fla.,; Ishikawa, E. et al., (eds.), 1981, Enzyme Immunoassay, Kgaku Shoin, Tokyo). The enzyme which is bound to the antibody will react with an appropriate substrate, preferably a chromogenic substrate, in such a manner as to produce a chemical moiety that can be detected, for example, by spectrophotometric, fluorimetric or by visual means. Enzymes that can be used to detectably label the antibody include, but are not limited to, malate dehydrogenase, staphylococcal nuclease, delta-5-steroid isomerase, yeast alcohol dehydrogenase, α-glycerophosphate, dehydrogenase, triose phosphate isomerase, horseradish peroxidase, alkaline phosphatase, asparaginase, glucose oxidase, β-galactosidase, ribonuclease, urease, catalase, glucose-6-phosphate dehydrogenase, glucoamylase and acetylcholinesterase. The detection can be accomplished by calorimetric methods that employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect Hcen-2 gene products through the use of a radioimmunoassay (RIA) (see, for example, Weintraub, B., Principles of Radioimmunoassays, Seventh Training Course on Radioligand Assay Techniques, The Endocrine Society, March, 1986). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

5.8. Screening Assays for Compounds that Modulate Hcen-2 Gene Activity

The following assays are designed to identify compounds that bind to an Hcen-2 gene product, compounds that bind to intracellular proteins, or portions of proteins that interact with an Hcen-2 gene product, compounds that interfere with the interaction of an Hcen-2 gene product with intracellular proteins and compounds that modulate the activity of the Hcen-2 gene (i.e., modulate the level of Hcen-2 gene expression and/or modulate the level of Hcen-2 gene product activity). Assays may additionally be utilized that identify compounds that bind to Hcen-2 gene regulatory sequences (e.g., promoter sequences; see e.g., Platt, 1994, J. Biol. Chem. 269, 28558–28562), and that can modulate the level of Hcen-2 gene expression. Such compounds may include, but are not limited to, small organic molecules, such as ones that are able to cross the blood-brain barrier, gain entry into an appropriate cell and affect expression of the Hcen-2 gene or some other gene involved in an Hcen-2 regulatory pathway, or intracellular proteins.

Methods for the identification of such intracellular proteins are described, below, in Section 5.8.2. Such intracellular proteins may be involved in the control and/or regulation of mood. Further, among these compounds are compounds that affect the level of Hcen-2 gene expression and/or Hcen-2 gene product activity and that can be used in the therapeutic treatment of Hcen-2 mediated disorders as described, below, in Section 5.9.

Compounds may include, but are not limited to, peptides such as, for example, soluble peptides, including but not limited to, Ig-tailed fusion peptides, and members of random peptide libraries; (see, e.g., Lam, et al., 1991, Nature 354, 82–84; Houghten, et al., 1991, Nature 354, 84–86), and combinatorial chemistry-derived molecular library made of D- and/or L- configuration amino acids, phosphopeptides (including, but not limited to members of random or partially degenerate, directed phosphopeptide libraries; see, e.g., Songyang, et al., 1993, Cell 72, 767–778), antibodies (including, but not limited to, polyclonal, monoclonal, humanized, anti-idiotypic, chimeric or single chain antibodies, and FAb, F(ab')$_2$ and FAb expression library fragments and epitope-binding fragments thereof), and small organic or inorganic molecules.

Such compounds may further comprise compounds, in particular drugs or members of classes or families of drugs, known to ameliorate or exacerbate the symptoms of an Hcen-2 mediated disorder. Such compounds include antidepressants such as lithium salts, carbamazepine, valproic acid, lysergic acid diethylamide (LSD), p-chlorophenylalanine, p-propyldopacetamide dithiocarbamate derivatives e.g., FLA 63; anti-anxiety drugs, e.g., diazepam; monoamine oxidase (MAO) inhibitors, e.g., iproniazid, clorgyline, phenelzine and isocarboxazid; biogenic amine uptake blockers, e.g., tricyclic antidepressants such as desipramine, imipramine and amitriptyline; serotonin reuptake inhibitors e.g., fluoxetine; antipsychotic drugs such as phenothiazine derivatives (e.g., chlorpromazine (thorazine) and trifluopromazine)), butyrophenones (e.g., haloperidol (Haldol)), thioxanthene derivatives (e.g., chlorprothixene), and dibenzodiazepines (e.g., clozapine); benzodiazepines; dopaminergic agonists and antagonists e.g., L-DOPA, cocaine, amphetamine, α-methyl-tyrosine, reserpine, tetrabenazine, benzotropine, pargyline; noradrenergic agonists and antagonists e.g., clonidine, phenoxybenzamine, phentolamine, tropolone.

Compounds identified via assays such as those described herein may be useful, for example, in elaborating the biological function of the Hcen-2 gene product and for ameliorating Hcen-2 mediated disorders. Assays for testing the effectiveness of compounds identified by, for example, techniques such as those described in Sections 5.8.1–5.8.3, are discussed, below, in Section 5.8.4.

5.8.1. In Vitro Screening Assays for Compounds That Bind to the Hcen-2 Gene Product In vitro systems may be designed to identify compounds capable of binding the Hcen-2 gene products of the invention. Compounds identified may be useful, for example, in modulating the activity of unimpaired and/or mutant Hcen-2 gene products, may be useful in elaborating the biological function of the Hcen-2 gene product, may be utilized in screens for identifying compounds that disrupt normal Hcen-2 gene product interactions, or may in themselves disrupt such interactions.

The principle of the assays used to identify compounds that bind to the Hcen-2 gene product involves preparing a reaction mixture of the Hcen-2 gene product and the test compound under conditions and for a time sufficient to allow the two components to interact and bind, thus forming a complex that can be removed and/or detected in the reaction mixture. These assays can be conducted in a variety of ways. For example, one method to conduct such an assay involves anchoring an Hcen-2 gene product or a test substance onto a solid support and detecting Hcen-2 gene product/test compound complexes formed on the solid support at the end of the reaction. In one embodiment of such a method, the Hcen-2 gene product may be anchored onto a solid support, and the test compound, which is not anchored, may be labeled, either directly or indirectly.

In practice, microtiter plates are conveniently utilized as the solid support. The anchored component may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the previously non-immobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for Hcen-2 gene product or the test compound to anchor any complexes formed in solution, and a labeled antibody specific for the other component of the possible complex to detect anchored complexes.

5.8.2. Assays for Intracellular Proteins that Interact with Hcen-2 Gene Products Any method suitable for detecting protein-protein interactions may be employed for identifying Hcen-2 gene product-protein interactions.

Among the traditional methods that may be employed are co-immunoprecipitation, cross-linking and co-purification through gradients or chromatographic columns. Utilizing procedures such as these allows for the identification of proteins, including intracellular proteins, that interact with Hcen-2 gene products. Once isolated, such a protein can be identified and can be used in conjunction with standard techniques, to identify proteins it interacts with. For example, at least a portion of the amino acid sequence of a protein that interacts with the Hcen-2 gene product can be ascertained using techniques well known to those of skill in the art, such as via the Edman degradation technique (see, e.g., Creighton, 1983, "Proteins: Structures and Molecular Principles," W. H. Freeman & Co., N.Y., pp.34–49). The amino acid sequence obtained may be used as a guide for the generation of oligonucleotide mixtures that can be used to screen for gene sequences encoding such proteins. Screening made be accomplished, for example, by standard hybridization or PCR techniques. Techniques for the generation of oligonucleotide mixtures and the screening are well-known. (See, e.g., Ausubel, supra, and 1990, "PCR Protocols: A Guide to Methods and Applications," Innis, et al., eds. Academic Press, Inc., New York).

Additionally, methods may be employed that result in the simultaneous identification of genes that encode a protein which interacts with an Hcen-2 gene product. These methods include, for example, probing expression libraries with labeled Hcen-2 gene product, using Hcen-2 gene product in a manner similar to the well known technique of antibody probing of λgt11 libraries.

One method that detects protein interactions in vivo, the two-hybrid system, is described in detail for illustration only and not by way of limitation. One version of this system has been described (Chien, et al., 1991, Proc. Natl. Acad. Sci. USA, 88, 9578–9582) and is commercially available from Clontech (Palo Alto, Calif.).

Briefly, utilizing such a system, plasmids are constructed that encode two hybrid proteins: one consists of the DNA-binding domain of a transcription activator protein fused to the Hcen-2 gene product and the other consists of the transcription activator protein's activation domain fused to an unknown protein that is encoded by a cDNA that has been recombined into this plasmid as part of a cDNA library. The DNA-binding domain fusion plasmid and the cDNA library are transformed into a strain of the yeast *Saccharomyces cerevisiae* that contains a reporter gene (e.g., HBS or lacZ) whose regulatory region contains the transcription activator's binding site. Either hybrid protein alone cannot activate transcription of the reporter gene: the DNA-binding domain hybrid cannot because it does not provide activation function and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodologies may be used to screen activation domain libraries for proteins that interact with the "bait" gene product. By way of example, and not by way of limitation, Hcen-2 gene products may be used as the bait gene product. Total genomic or cDNA sequences are fused to the DNA encoding an activation domain. This library and a plasmid encoding a hybrid of a bait Hcen-2 gene product fused to the DNA-binding domain are co-transformed into a yeast reporter strain, and the resulting transformants are screened for those that express the reporter gene. For example, a bait Hcen-2 gene sequence, such as the open reading frame of the Hcen-2 gene, can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with bait Hcen-2 gene product are to be detected can be made using methods routinely practiced in the art. According to the particular system described herein, for example, the cDNA fragments can be inserted into a vector such that they are translationally fused to the transcriptional activation domain of GAL4. Such a library can be co-transformed along with the bait Hcen-2 gene-GAL4 fusion plasmid into a yeast strain that contains a lacZ gene driven by a promoter that contains GAL4 activation sequence. A cDNA encoded protein, fused to a GAL4 transcriptional activation domain that interacts with bait Hcen-2 gene product will reconstitute an active GAL4 protein and thereby drive expression of the HIS3 gene. Colonies that express HIS3 can be detected by their growth on petri dishes containing semi-solid agar based media lacking histidine. The cDNA can then be purified from these strains, and used to produce and isolate the bait Hcen-2 gene product-interacting protein using techniques routinely practiced in the art.

5.8.3. Assays for Compounds that Interfere with Hcen-2 Gene Product Macromolecule Interaction The Hcen-2 gene products may, In vivo, interact with one or more macromolecules, including intracellular macromolecules, such as proteins. Such macromolecules may include, but are not limited to, nucleic acid molecules and those proteins identified via methods such as those described, above, in Sections 5.8.1–5.8.2. For purposes of this discussion, the macromolecules are referred to herein as "binding partners". Compounds that disrupt Hcen-2 gene product binding to a binding partner may be useful in regulating the activity of the Hcen-2 gene product, especially mutant Hcen-2 gene products. Such compounds may include, but are not limited to molecules such as peptides, and the like, as described, for example, in Section 5.8.2 above.

The basic principle of an assay system used to identify compounds that interfere with the interaction between the Hcen-2 gene product and a binding partner or partners involves preparing a reaction mixture containing the Hcen-2 gene product and the binding partner under conditions and for a time sufficient to allow the two to interact and bind, thus forming a complex. In order to test a compound for inhibitory activity, the reaction mixture is prepared in the presence and absence of the test compound. The test compound may be initially included in the reaction mixture, or may be added at a time subsequent to the addition of Hcen-2 gene product and its binding partner. Control reaction mixtures are incubated without the test compound or with a compound which is known not to block complex formation. The formation of any complexes between the Hcen-2 gene product and the binding partner is then detected. The formation of a complex in the control reaction, but not in the reaction mixture containing the test compound, indicates that the compound interferes with the interaction of the Hcen-2 gene product and the binding partner. Additionally, complex formation within reaction mixtures containing the test compound and normal Hcen-2 gene product may also be compared to complex formation within reaction mixtures containing the test compound and a mutant Hcen-2 gene product. This comparison may be important in those cases wherein it is desirable to identify compounds that disrupt interactions of mutant but not normal Hcen-2 gene product.

The assay for compounds that interfere with the interaction of the Hcen-2 gene products and binding partners can be conducted in a heterogeneous or homogeneous format. Heterogeneous assays involve anchoring either the Hcen-2 gene product or the binding partner onto a solid support and detecting complexes formed on the solid support at the end of the reaction. In homogeneous assays, the entire reaction is carried out in a liquid phase. In either approach, the order of addition of reactants can be varied to obtain different information about the compounds being tested. For examples, test compounds that interfere with the interaction between the Hcen-2 gene products and the binding partners, e.g., by competition, can be identified by conducting the reaction in the presence of the test substance; i.e., by adding the test substance to the reaction mixture prior to or simultaneously with the Hcen-2 gene product and interactive intracellular binding partner. Alternatively, test compounds that disrupt preformed complexes, e.g., compounds with higher binding constants that displace one of the components from the complex, can be tested by adding the test compound to the reaction mixture after complexes have been formed. The various formats are described briefly below.

In a heterogeneous assay system, either the Hcen-2 gene product or the interactive binding partner, is anchored onto a solid surface, while the non-anchored species is labeled, either directly or indirectly. In practice, microtiter plates are conveniently utilized. The anchored species may be immobilized by non-covalent or covalent attachments. Non-covalent attachment may be accomplished simply by coating the solid surface with a solution of the Hcen-2 gene product or binding partner and drying. Alternatively, an immobilized antibody specific for the species to be anchored may be used to anchor the species to the solid surface. The surfaces may be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, may be directly labeled or indirectly labeled with a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex formation or that disrupt preformed complexes can be identified.

In an alternate embodiment of the invention, a homogeneous assay can be used. In this approach, a preformed complex of the Hcen-2 gene product and the interactive binding partner is prepared in which either the Hcen-2 gene product or its binding partners is labeled, but the signal generated by the label is quenched due to complex formation (see, e.g., U.S. Pat. No. 4,109,496 by Rubenstein which utilizes this approach for immunoassays). The addition of a test substance that competes with and displaces one of the species from the preformed complex will result in the generation of a signal above background. In this way, test substances that disrupt Hcen-2 gene product/binding partner interaction can be identified.

In another embodiment of the invention, these same techniques can be employed using peptide fragments that correspond to the binding domains of the Hcen-2 product and/or the binding partner (in cases where the binding partner is a protein), in place of one or both of the full length proteins. Any number of methods routinely practiced in the art can be used to identify and isolate the binding sites. These methods include, but are not limited to, mutagenesis of the gene encoding one of the proteins and screening for disruption of binding in a co-immunoprecipitation assay. Compensating mutations in the gene encoding the second species in the complex can then be selected. Sequence analysis of the genes encoding the respective proteins will reveal the mutations that correspond to the region of the protein involved in interactive binding. Alternatively, one protein can be anchored to a solid surface using methods described in this Section above, and allowed to interact with and bind to its labeled binding partner, which has been treated with a proteolytic enzyme, such as trypsin. After washing, a short, labeled peptide comprising the binding domain may remain associated with the solid material, which can be isolated and identified by amino acid sequencing. Also, once the gene coding for the segments is engineered to express peptide fragments of the protein, it can then be tested for binding activity and purified or synthesized.

For example, and not by way of limitation, an Hcen-2 gene product can be anchored to a solid material as described, above, in this Section by making a GST-Hcen-2 fusion protein and allowing it to bind to glutathione agarose beads. The binding partner can be labeled with a radioactive isotope, such as $^{35}S$, and cleaved with a proteolytic enzyme such as trypsin. Cleavage products can then be added to the anchored GST-Hcen-2 fusion protein and allowed to bind. After washing away unbound peptides, labeled bound material, representing the binding partner binding domain, can be eluted, purified, and analyzed for amino acid sequence by well-known methods. Peptides so identified can be produced synthetically or produced using recombinant DNA technology.

5.8.4. Assays for Identification of Compounds that Ameliorate an Hcen-2 Mediated Disorder Compounds, including but not limited to binding compounds identified via assay techniques such as those described, above, in Sections 5.8.1–5.8.4, can be tested for the ability to ameliorate symptoms of an Hcen-2 mediated disorder.

It should be noted that the assays described herein can identify compounds that affect Hcen-2 activity by either affecting Hcen-2 gene expression or by affecting the level of Hcen-2 gene product activity. For example, compounds may be identified that are involved in another step in the pathway in which the Hcen-2 gene and/or Hcen-2 gene product is involved and, by affecting this same pathway may modulate the effect of Hcen-2 on the development of an Hcen-2 mediated disorder. Such compounds can be used as part of a therapeutic method for the treatment of the disorder.

Described below are, cell-based and animal model-based assays for the identification of compounds exhibiting such an ability to ameliorate symptoms of an Hcen-2 mediated disorder.

First, cell-based systems can be used to identify compounds that may act to ameliorate symptoms of an Hcen-2 mediated disorder. Such cell systems can include, for example, recombinant or non-recombinant cell, such as cell lines, that express the Hcen-2 gene.

In utilizing such cell systems, cells that express Hcen-2 may be exposed to a compound suspected of exhibiting an ability to ameliorate symptoms of an Hcen-2 mediated disorder, at a sufficient concentration and for a sufficient time to elicit such an amelioration of such symptoms in the exposed cells. After exposure, the cells can be assayed to measure alterations in the expression of the Hcen-2 gene, e.g., by assaying cell lysates for Hcen-2 mRNA transcripts (e.g., by Northern analysis) or for Hcen-2 gene products expressed by the cell; compounds that modulate expression of the Hcen-2 gene are good candidates as therapeutics.

In addition, animal-based systems or models for an Hcen-2 mediated disorder, for example, transgenic mice containing a human or altered form of Hcen-2 gene, may be used to identify compounds capable of ameliorating symptoms of the disorder. Such animal models may be used as test substrates for the identification of drugs, pharmaceuticals, therapies and interventions. For example, animal models may be exposed to a compound suspected of exhibiting an ability to ameliorate symptoms, at a sufficient concentration and for a sufficient time to elicit such an amelioration of symptoms of an Hcen-2 mediated disorder. The response of the animals to the exposure may be monitored by assessing the reversal of the symptoms of the disorder.

With regard to intervention, any treatments that reverse any aspect of symptoms of an Hcen-2 mediated disorder, should be considered as candidates for human therapeutic intervention in such a disorder. Dosages of test agents may be determined by deriving dose-response curves, as discussed in Section 5.10.1, below.

5.9. Compounds and Methods for the Treatment of Hcen-2 Mediated Disorders

Described below are methods and compositions whereby an Hcen-2 mediated disorder, may be treated. For example, such methods can comprise administering compounds which modulate the expression of a mammalian Hcen-2 gene and/or the synthesis or activity of a mammalian Hcen-2 gene product so symptoms of the disorder are ameliorated.

Alternatively, in those instances whereby the mammalian Hcen-2 mediated disorders result from Hcen-2 gene mutations, such methods can comprise supplying the mammal with a nucleic acid molecule encoding an unimpaired Hcen-2 gene product such that an unimpaired Hcen-2 gene product is expressed and symptoms of the disorder are ameliorated.

In another embodiment of methods for the treatment of mammalian Hcen-2 mediated disorders resulting from Hcen-2 gene mutations, such methods can comprise supplying the mammal with a cell comprising a nucleic acid molecule that encodes an unimpaired Hcen-2 gene product such that the cell expresses the unimpaired Hcen-2 gene product and symptoms of the disorder are ameliorated.

In cases in which a loss of normal Hcen-2 gene product function results in the development of a Hcen-2 mediated disorder an increase in Hcen-2 gene product activity would facilitate progress towards an asymptomatic state in individuals exhibiting a deficient level of Hcen-2 gene expression and/or Hcen-2 gene product activity. Methods for enhancing the expression or synthesis of Hcen-2 can include, for example, methods such as those described below, in Section 5.9.2.

Alternatively, symptoms of Hcen-2 mediated disorders, may be ameliorated by administering a compound that decreases the level of Hcen-2 gene expression and/or Hcen-2 gene product activity. Methods for inhibiting or reducing the level of Hcen-2 gene product synthesis or expression can include, for example, methods such as those described in Section 5.9.1.

5.9.1. Inhibitory Antisense, Ribozyme and Triple Helix Approaches

In another embodiment, symptoms of Hcen-2 mediated disorders may be ameliorated by decreasing the level of Hcen-2 gene expression and/or Hcen-2 gene product activity by using Hcen-2 gene sequences in conjunction with well-known antisense, gene "knock-out," ribozyme and/or triple helix methods to decrease the level of Hcen-2 gene expression. Among the compounds that may exhibit the ability to modulate the activity, expression or synthesis of the Hcen-2 gene, including the ability to ameliorate the symptoms of a Hcen-2 mediated disorder, are antisense, ribozyme, and triple helix molecules. Such molecules may be designed to reduce or inhibit either unimpaired, or if appropriate, mutant target gene activity. Techniques for the production and use of such molecules are well known to those of skill in the art.

Antisense RNA and DNA molecules act to directly block the translation of mRNA by hybridizing to targeted mRNA and preventing protein translation. Antisense approaches involve the design of oligonucleotides that are complementary to a target gene mRNA. The antisense oligonucleotides will bind to the complementary target gene mRNA transcripts and prevent translation. Absolute complementarity, although preferred, is not required.

A sequence "complementary" to a portion of an RNA, as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

In one embodiment, oligonucleotides complementary to non-coding regions of the Hcen-2 gene could be used in an antisense approach to inhibit translation of endogenous Hcen-2 mRNA. Antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger, et al., 1989, Proc. Natl. Acad. Sci. U.S.A. 86, 6553–6556; Lemaitre, et al., 1987, Proc. Natl. Acad. Sci. U.S.A. 84, 648–652; PCT Publication No. WO88/09810, published Dec. 15, 1988) or the blood-brain barrier (see, e.g., PCT Publication No. WO89/10134, published Apr. 25, 1988), hybridization-triggered cleavage agents (see, e.g., Krol et al., 1988, BioTechniques 6, 958–976) or intercalating agents (see, e.g., Zon, 1988, Pharm. Res. 5, 539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group including but not limited to arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier, et al., 1987, Nucl. Acids Res. 15, 6625–6641). The oligonucleotide is a 2'-O-methylribonucleotide (Inoue, et al., 1987, Nucl. Acids Res. 15, 6131–6148), or a chimeric RNA-DNA analogue (Inoue, et al., 1987, FEBS Lett. 215, 327–330). oligonucleotides of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein, et al. (1988, Nucl. Acids Res. 16, 3209), methylphosphonate oligonucleotides can be prepared by use of controlled pore glass polymer supports (Sarin, et al., 1988, Proc. Natl. Acad. Sci. U.S.A. 85, 7448–7451), etc.

While antisense nucleotides complementary to the target gene coding region sequence could be used, those complementary to the transcribed, untranslated region are most preferred.

Antisense molecules should be delivered to cells that express the target gene in vivo. A number of methods have been developed for delivering antisense DNA or RNA to cell; e.g., antisense molecules can be injected directly into the tissue site, or modified antisense molecules, designed to target the desired cells (e.g., antisense linked to peptides or antibodies that specifically bind receptors or antigens; expressed on the target cell surface) can be administered systemically.

However, it is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous target gene transcripts and thereby prevent translation of the target gene mRNA. For example, a vector can be introduced e.g., such that it is taken up by a cell and directs the transcription of an antisense RNA. Such a vector can remain episomal or become chromosomally integrated, as long as it can be transcribed to produce the desired antisense RNA. Such vectors can be constructed by is recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, Nature 290, 304–310), the promoter contained in the 3' long terminal repeat of Rous sarcoma virus (Yamamoto, et al., 1980, Cell 22, 787–797), the herpes thymidine kinase promoter (Wagner, et al., 1981, Proc. Natl. Acad. Sci. U.S.A. 78, 1441–1445), the regulatory sequences of the metallothionein gene (Brinster, et al., 1982, Nature 296, 39–42), etc. Any type of plasmid, cosmid, YAC or viral vector can be used to prepare the recombinant DNA construct which can be introduced directly into the tissue site. Alternatively, viral vectors can be used that selectively infect the desired tissue, in which case administration may be accomplished by another route (e.g., systemically).

Ribozyme molecules designed to catalytically cleave target gene mRNA transcripts can also be used to prevent translation of target gene mRNA and, therefore, expression of target gene product. (See, e.g., PCT International Publication WO90/11364, published Oct. 4, 1990; Sarver, et al., 1990, Science 247, 1222–1225).

Ribozymes are enzymatic RNA molecules capable of catalyzing the specific cleavage of RNA. (For a review, see Rossi, 1994, Current Biology 4, 469–471). The mechanism of ribozyme action involves sequence specific hybridization of the ribozyme molecule to complementary target RNA, followed by an endonucleolytic cleavage event. The composition of ribozyme molecules must include one or more sequences complementary to the target gene mRNA, and must include the well known catalytic sequence responsible for mRNA cleavage. For this sequence, see, e.g., U.S. Pat. No. 5,093,246, which is incorporated herein by reference in its entirety. While ribozymes that cleave mRNA at site specific recognition sequences can be used to destroy target gene mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Myers, 1995, *Molecular Biology and Biotechnology: A Comprehensive Desk Reference,* VCH Publishers, New York, (see especially FIG. 4, page 833) and in Haseloff and Gerlach, 1988, Nature, 334, 585–591, which is incorporated herein by reference in its entirety.

Preferably the ribozyme is engineered so that the cleavage recognition site is located near the 5' end of the target gene mRNA, i.e., to increase efficiency and minimize the intracellular accumulation of non-functional mRNA transcripts.

The ribozymes of the present invention also include RNA endoribonucleases (hereinafter "Cech-type ribozymes") such as the one that occurs naturally in *Tetrahymena thermophila* (known as the IVS, or L-19 IVS RNA) and that has been extensively described by Thomas Cech and collaborators (Zaug, et al., 1984, Science, 224, 574–578; Zaug and Cech, 1986, Science, 231, 470–475; Zaug, et al., 1986, Nature, 324, 429–433; published International patent application No. WO 88/04300 by University Patents Inc.; Been and Cech, 1986, Cell, 47, 207–216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in the target gene.

As in the antisense approach, the ribozymes can be composed of modified oligonucleotides (e.g., for improved stability, targeting, etc.) and should be delivered to cells that express the target gene in vivo. A preferred method of delivery involves using a DNA construct "encoding" the ribozyme under the control of a strong constitutive pol III or pol II promoter, so that transfected cells will produce sufficient quantities of the ribozyme to destroy endogenous target gene messages and inhibit translation. Because ribozymes unlike antisense molecules, are catalytic, a lower intracellular concentration is required for efficiency.

Endogenous target gene expression can also be reduced by inactivating or "knocking out" the target gene or its promoter using targeted homologous recombination (e.g., see Smithies, et al., 1985, Nature 317, 230–234; Thomas and Capecchi, 1987, Cell 51, 503–512; Thompson, et al., 1989, Cell 5, 313–321; each of which is incorporated by reference herein in its entirety). For example, a mutant, non-functional target gene (or a completely unrelated DNA sequence) flanked by DNA homologous to the endogenous target gene (either the coding regions or regulatory regions of the target gene) can be used, with or without a selectable marker and/or a negative selectable marker, to transfect cells that express the target gene in vivo. Insertion of the DNA construct, via targeted homologous recombination, results in inactivation of the target gene. Such approaches are particularly suited in the agricultural field where. modifications to ES (embryonic stem) cells can be used to generate animal offspring with an inactive target gene (e.g., see Thomas and Capecchi, 1987 and Thompson, 1989, supra). However this approach can be adapted for use in humans provided the recombinant DNA constructs are directly administered or targeted to the required site in vivo using appropriate viral vectors.

Alternatively, endogenous target gene expression can be reduced by targeting deoxyribonucleotide sequences complementary to the regulatory region of the target gene (i.e., the target gene promoter and/or enhancers) to form triple helical structures that prevent transcription of the target gene in target cells in the body. (See generally, Helene, 1991, Anticancer Drug Des., 6(6), 569–584; Helene, et al., 1992, Ann. N.Y. Acad. Sci., 660, 27–36; and Maher, 1992, Bioassays 14(12), 807–815).

Nucleic acid molecules to be used in triplex helix formation for the inhibition of transcription should be single stranded and composed of deoxynucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and CGC$^+$ triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, contain a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

In instances wherein the antisense, ribozyme, and/or triple helix molecules described herein are utilized to inhibit mutant gene expression, it is possible that the technique may so efficiently reduce or inhibit the transcription (triple helix) and/or translation (antisense, ribozyme) of mRNA produced by normal target gene alleles that the possibility may arise wherein the concentration of normal target gene product present may be lower than is necessary for a normal phenotype. In such cases, to ensure that substantially normal levels of target gene activity are maintained, therefore, nucleic acid molecules that encode and express target gene polypeptides exhibiting normal target gene activity may, be introduced into cells via gene therapy methods such as those described, below, in Section 5.9.2 that do not contain sequences susceptible to whatever antisense, ribozyme, or triple helix treatments are being utilized. Alternatively, in instances whereby the target gene encodes an extracellular protein, it may be preferable to co-administer normal target gene protein in order to maintain the requisite level of target gene activity.

Anti-sense RNA and DNA, ribozyme, and triple helix molecules of the invention may be prepared by any method known in the art for the synthesis of DNA and RNA molecules, as discussed above. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

5.9.2. Gene Replacement Therapy

Hcen-2 gene nucleic acid sequences, described above in Section 5.1, can be utilized for the treatment of an Hcen-2 mediated disorder. Such treatment can be in the form of gene replacement therapy. Specifically, one or more copies of a normal Hcen-2 gene or a portion of the Hcen-2 gene that directs the production of an Hcen-2 gene product exhibiting normal Hcen-2 gene function, may be inserted into the appropriate cells within a patient, using vectors that include, but are not limited to adenovirus, adeno-associated virus, and retrovirus vectors, in addition to other particles that introduce DNA into cells, such as liposomes.

Because the Hcen-2 gene is expressed in the brain, such gene replacement therapy techniques should be capable delivering Hcen-2 gene sequences to these cell types within patients. Thus, in one embodiment, techniques that are well known to those of skill in the art (see, e.g., PCT Publication No. WO89/10134, published Apr. 25, 1988) can be used to enable Hcen-2 gene sequences to cross the blood-brain barrier readily and to deliver the sequences to cells in the brain. With respect to delivery that is capable of crossing the blood-brain barrier, viral vectors such as, for example, those described above, are preferable.

In another embodiment, techniques for delivery involve direct administration of such Hcen-2 gene sequences to the site of the cells in which the Hcen-2 gene sequences are to be expressed.

Additional methods that may be utilized to increase the overall level of Hcen-2 gene expression and/or Hcen-2 gene product activity include the introduction of appropriate Hcen-2 -expressing cells, preferably autologous cells, into a patient at positions and in numbers that are sufficient to ameliorate the symptoms of an Hcen-2 mediated disorder. Such cells may be either recombinant or non-recombinant.

Among the cells that can be administered to increase the overall level of Hcen-2 gene expression in a patient are normal cells, preferably brain cells, that express the Hcen-2 gene. Alternatively, cells, preferably autologous cells, can be engineered to express Hcen-2 gene sequences, and may then be introduced into a patient in positions appropriate for the amelioration of the symptoms of an Hcen-2 mediated disorder. Alternately, cells that express an unimpaired Hcen-2 gene and that are from a MHC matched individual can be utilized, and may include, for example, brain cells. The expression of the Hcen-2 gene sequences is controlled by the appropriate gene regulatory sequences to allow such expression in the necessary cell types. Such gene regulatory sequences are well known to the skilled artisan. Such cell-based gene therapy techniques are well known to those skilled in the art, see, e.g., Anderson, U.S. Pat. No. 5,399,349.

When the cells to be administered are non-autologous cells, they can be administered using well known techniques that prevent a host immune response against the introduced cells from developing. For example, the cells may be introduced in an encapsulated form which, while allowing for an exchange of components with the immediate extracellular environment, does not allow the introduced cells to be recognized by the host immune system.

Additionally, compounds, such as those identified via techniques such as those described, above, in Section 5.8, that are capable of modulating Hcen-2 gene product activity can be administered using standard techniques that are well known to those of skill in the art. In instances in which the compounds to be administered are to involve an interaction with brain cells, the administration techniques should include well known ones that allow for a crossing of the blood-brain barrier.

5.10. Pharmaceutical Preparations and Methods of Administration

The compounds that are determined to affect Hcen-2 gene expression or gene product activity can be administered to a patient at therapeutically effective doses to treat or ameliorate an Hcen-2 mediated disorder. A therapeutically effective dose refers to that amount of the compound sufficient to result in amelioration of symptoms of such a disorder.

5.10.1. Effective Dose

Toxicity and therapeutic efficacy of such compounds can be determined by standard pharmaceutical procedures in cell cultures or experimental animals, e.g., for determining the $LD_{50}$ (the dose lethal to 50% of the population) and the EDS (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

Formulations and Use

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example,. as a sparingly soluble salt.

The compositions may, if desired, be presented in a pack or dispenser device that may contain one or more unit dosage forms containing the active ingredient. The pack may for example comprise metal or plastic foil, such as a blister pack. The pack or dispenser device may be accompanied by instructions for administration.

6. EXAMPLE

Localization of the Hcen-2 Gene to Chromosome 18

In the Example presented in this Section, studies are described that, first, define an interval approximately 310 kb on the short arm of human chromosome 18 within which a region associated with a neuropsychiatric disorder is located and, second, to the identification of the Hcen-2 gene, as mapping within this region.

6.1. Materials and Methods

6.1.1. Linkage Disequilibrium

Linkage disequilibrium (LD) studies were performed using DNA from a population sample of neuropsychiatric disorder (BP-I) patients. The population sample and LD techniques were as described in Freimer et al., 1996, Nature Genetics 12:436–441. The present LD study took advantage of the additional physical markers identified via the physical mapping techniques described below.

6.1.2. Yeast Artificial Chromosome (YAC) Mapping

For physical mapping, yeast artificial chromosomes (YACs) containing human sequences were mapped to the region being analyzed based on publicly available maps (Cohen et al., 1993, C.R. Acad. Sci. 316, 1484–1488). The YACs were then ordered and contig reconstructed by performing standard short tag sequence (STS)-content mapping with microsatellite markers and non-polymorphic STSs available from databases that surround the genetically defined candidate region.

6.1.3. Bacterial Artificial Chromosome (BAC) Mapping

STSs from the short arm of human chromosome 18 were used to screen a human BAC library (Research Genetics, Huntsville, Ala.). The ends of the BACs were cloned or directly sequenced. The end sequences were used to amplify the next overlapping BACs. From each BAC, additional microsatellites were identified. Specifically, random sheared libraries were prepared from overlapping BACs within the defined genetic interval. BAC DNA was sheared with a nebulizer (CIS-US Inc., Bedford, Mass.). Fragments in the size range of 600 to 1,000 bp were utilized for the sublibrary production. Microsatellite sequences from the sublibraries were identified by corresponding microsatellite probes. Sequences around such repeats were obtained to enable development of PCR primers for genomic DNA.

6.1.4. Radiation Hybrid (RH) Mapping

Standard RH mapping techniques were applied to a Stanford G3 RH mapping panel (Research Genetics, Huntsville, Ala.) to order all microsatellite markers and non-polymorphic STSs in the region being analyzed.

6.1.5. Sample Sequencing

Random sheared libraries were made from all the BACs within the defined genetic region. Approximately 9,000 subclones within the approximately 310 kb region were sequenced with vector primers in order to achieve an 8-fold sequence coverage of the region. All sequences were processed through an automated sequence analysis pipeline that assessed quality, removed vector sequences and masked repetitive sequences. The resulting sequences were then compared to public DNA and protein databases using BLAST algorithms (Altschul, et al., 1990, J. Molec. Biol., 215, 403–410).

6.2. Results

Genetic regions involved in bipolar affective disorder (BAD) human genes had previously been reported to map to portions of the long (18q) and short (18p) arms of human chromosome 18, including a broad 18q genetic region of about 6–7 cM between markers D18S469 and D18S554 (U.S. Provisional Applications Serial Nos. 60/014,498 and 60/023,438, filed on Mar. 28, 1996 and Aug. 23, 1996, respectively, the entire contents of each of which are incorporated herein by reference; Preimer, et al., 1996, Neuropsychiat. Genet. 67, 254–263; Freimer, et al., 1996, Nature Genetics 12, 436–441), the entire contents of each of which are incorporated herein by reference.

Linkage Disequilibrium. Prior to attempting to identify gene sequences, studies were performed to further narrow the neuropsychiatric disorder region. Specifically, a linkage disequilibrium (LD) analysis was performed using population samples and techniques as described in Section 6.1, above, which took advantage of the additional physical markers identified via the physical mapping techniques described below.

High resolution physical mapping using YAC, BAC and RH techniques. In order to provide the precise order of genetic markers necessary for linkage and LD mapping, and to guide new microsatellite marker development for finer mapping, a high resolution physical map of the 18q23 candidate region was developed using YAC, BAC and RH techniques.

For such physical mapping, first, YACs were mapped to the chromosome 18 region being analyzed. Using the mapped YAC contig as a framework, the region from publicly available markers D18S1161 and D18S554, which spans most of the D18S469–D18S554 region described above, was also mapped and contiged with BACs. Sublibraries from the contiged BACs were constructed, from which microsatellite marker sequences were identified and sequenced.

To ensure development of an accurate physical map, the radiation hybrid (RH) mapping technique was independently applied to the region being analyzed. RH was used to order all microsatellite markers and non-polymorphic STSs in the region. Thus, the high resolution physical map ultimately constructed was obtained using data from RH mapping and STS-content mapping.

BAC clones within the newly identified 310 kb neuropsychiatric disorder region were analyzed to identify specific genes within the region. A combination of sample sequencing, cDNA selection and transcription mapping analyses; were combined to arrange sequences into tentative transcription units, that is, tentatively delineating the coding sequences of genes within this genomic region of interest. One of the transcription units identified was termed Hcen-2.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparen to those skilled in the art from the foregoing description and accompanying drawings. Such modifications are intended to fall within the scope of the appended claims.

All publications and patent applications mentioned in this specification are herein incorporated by reference to the same extent as if each individual publication or patent application was specifically and individually indicated to be incorporated by reference.

What is claimed is:

1. A method for identifying a compound to be tested for an ability to treat a human centrin (Hcen-2)-mediated neuropsychiatric disorder, comprising the steps of:
   a) contacting a test compound with a human centrin (Hcen-2) protein;
   b) determining whether said test compound binds to said human centrin Hcen-2) protein; and
   c) selecting a test compound that binds to said human centrin (Hcen-2) protein as being a compound that can be used to treat a human centrin (Hcen-2)-mediated neuropsychiatric disorder.

2. The method of claim 1, wherein a human centrin (Hcen-2) protein comprises the amino acid sequence of SEQ ID NO: 2.

3. The method of claim 1, wherein a human centrin (Hcen-2) protein having an altered activity is used.

4. A method for identifying compounds to be tested for an ability to treat a human centrin (Hcen-2)-mediated neuropsychiatric disorder comprising the steps of:
   a) incubating a cell that expresses a human centrin (Hcen-2) gene in the presence and absence of a test compound;
   b) determining the activity of the human centrin (Hcen-2) gene product in the presence and absence of said test compound; and
   c) selecting a test compound that alters the activity of said human centrin (Hcen-2) gene product as being a compound that can be used to treat a human centrin gene (Hcen-2)-mediated neuropsychiatric disorder.

5. The method of claim 4, wherein a human centrin gene (Hcen-2) product comprises the amino acid sequence of SEQ ID NO: 2.

6. The method of claim 4, wherein a human centrin gene (Hcen-2) product having an altered activity is used.

* * * * *

SEQUENCE LISTING

```
<160> NUMBER OF SEQ ID NOS: 3

<210> SEQ ID NO 1
<211> LENGTH: 1173
<212> TYPE: DNA
<213> ORGANISM: Homo sapiens
<220> FEATURE:
<221> NAME/KEY: CDS
<222> LOCATION: (49)..(564)

<400> SEQUENCE: 1
gaattcgggg ggcggtgccg ttgggaccac ggcggccaga gcggcagg atg gct tcc      57
                                                    Met Ala Ser
                                                      1 ggc ttc aag aag ccc agc gct gcc tcc acc ggc caa aag aga aag gtg    105
Gly Phe Lys Lys Pro Ser Ala Ala Ser Thr Gly Gln Lys Arg Lys Val
      5                  10                  15 gca cct aag ccc gag ctc act gag gat cag aag caa gaa gtt cgg gaa    153
Ala Pro Lys Pro Glu Leu Thr Glu Asp Gln Lys Gln Glu Val Arg Glu
```

```
                 20                    25                     30                    35
gca ttt gac ctc ttc gac gtg gac gga agt ggg acc atc gac gcg aag            201
Ala Phe Asp Leu Phe Asp Val Asp Gly Ser Gly Thr Ile Asp Ala Lys
             40                           45                      50 gag ctg aag gtg gcc atg aga gcg ctg ggc ttc gaa ccc agg aag gaa            249
Glu Leu Lys Val Ala Met Arg Ala Leu Gly Phe Glu Pro Arg Lys Glu
                 55                      60                     65 gag atg aag aaa atg atc tcc gag gtg gac agg gaa ggc acg ggg aag            297
Glu Met Lys Lys Met Ile Ser Glu Val Asp Arg Glu Gly Thr Gly Lys
         70                       75                      80 atc agc ttc aat gac ttc ctg gcc gtg atg acg cag aag atg tcc gag            345
Ile Ser Phe Asn Asp Phe Leu Ala Val Met Thr Gln Lys Met Ser Glu
             85                       90                      95 aag gac acc aaa gaa gaa atc ctg aag gcc ttc agg ctc ttt gat gac            393
Lys Asp Thr Lys Glu Glu Ile Leu Lys Ala Phe Arg Leu Phe Asp Asp
100                 105                      110                     115 gat gag acc ggg aag atc tcg ttc aaa aac ctg aag cgt gtg gcc aac            441
Asp Glu Thr Gly Lys Ile Ser Phe Lys Asn Leu Lys Arg Val Ala Asn
                 120                     125                     130 gag ctg ggg gag aac ctc acg gat gag gag ctg cag gag atg atc gac            489
Glu Leu Gly Glu Asn Leu Thr Asp Glu Glu Leu Gln Glu Met Ile Asp
             135                     140                     145 gaa gct gat cgg gat ggg gac ggc gaa gtg aac gag gag gag ttc ctt            537
Glu Ala Asp Arg Asp Gly Asp Gly Glu Val Asn Glu Glu Glu Phe Leu
         150                     155                     160 cgg atc atg aag aag acc agc ctt tac tgaagtcggt tcagaagcta                  584
Arg Ile Met Lys Lys Thr Ser Leu Tyr
165                 170 aagtgactct ctgggttgcc tgcttccatt ttgtgaaacc ttagaggaca gcggctgcct          644
gtcccttctt cacccctca cccccataat ttgtctagat ctatttccat atctctagtt           704
caataataga atttgaaaga tgcttgtaat gtgagttttg ggttttaatt ctcaagagcc          764
aacctggagc acatgaggtt aaacaaaggg ccctgaagtt tgagtgcgcc ctccatttgc          824
cctgtgctga acttgctgtt catctgttga tctggaggca ggacagcttc tgggacacac          884
aaaaatgtgg ttccctttgt cacttctttg gtggtcttaa attatcttgc ttcatatatc          944
attccttaaa ttccagtcat tgttccagca taatgagatg gaatctgcca gtagatttgc          1004
ctagcctgtc cacttagctg aataccagtt tgaaggaaaa cagggtggcc acttacaaac          1064
ttacggagct caggacagat attcttataa agaatagact tgcttgggtg gtagtacgtt          1124
gtgcaatttt gactattcac tggctttata cctgcaaatg cccgaattc                      1173

<210> SEQ ID NO 2
<211> LENGTH: 172
<212> TYPE: PRT
<213> ORGANISM: Homo sapiens

<400> SEQUENCE: 2

Met Ala Ser Gly Phe Lys Lys Pro Ser Ala Ser Thr Gly Gln Lys
  1               5                  10                  15

Arg Lys Val Ala Pro Lys Pro Glu Leu Thr Glu Asp Gln Lys Gln Glu
                 20                  25                  30

Val Arg Glu Ala Phe Asp Leu Phe Asp Val Asp Gly Ser Gly Thr Ile
             35                  40                  45

Asp Ala Lys Glu Leu Lys Val Ala Met Arg Ala Leu Gly Phe Glu Pro
         50                  55                  60

Arg Lys Glu Glu Met Lys Lys Met Ile Ser Glu Val Asp Arg Glu Gly
```

-continued

```
                65                  70                  75                  80
            Thr Gly Lys Ile Ser Phe Asn Asp Phe Leu Ala Val Met Thr Gln Lys
                                85                  90                  95
            Met Ser Glu Lys Asp Thr Lys Glu Glu Ile Leu Lys Ala Phe Arg Leu
                            100                 105                 110
            Phe Asp Asp Asp Glu Thr Gly Lys Ile Ser Phe Lys Asn Leu Lys Arg
                        115                 120                 125
            Val Ala Asn Glu Leu Gly Glu Asn Leu Thr Asp Glu Glu Leu Gln Glu
                    130                 135                 140
            Met Ile Asp Glu Ala Asp Arg Asp Gly Asp Gly Glu Val Asn Glu Glu
            145                 150                 155                 160
            Glu Phe Leu Arg Ile Met Lys Lys Thr Ser Leu Tyr
                            165                 170

<210> SEQ ID NO 3
<211> LENGTH: 6709
<212> TYPE: DNA
<213> ORGANISM: Homo sapiens

<400> SEQUENCE: 3
aagcttcagc aggccaggat ttaaatccca gagccaccat ttattggcca tgtaccatta      60
aatatgtgtt acaggcctct cctgggcctc attttttttca tctgcaaaat aggaaatgat    120
ggcaaggatc aaataagatg acaactatga gaagcacgcc caaagctagg cacacattaa    180
atgtgtttcc cttcccttct taagtcagag tttggactct gaacataatg tactcccacc    240
aagagctgac tgtgactatg gcactgtttt ctatgaaggg agctcttggt ggcccttttgt   300 tgtaactgtt gattgcacac atctggaaac catgacaacc gttttgcttt tagttcagct    360
tggcccaaat gtagctctat ataaggcagc ttccatactt cagttttttcc caacacatca   420 tagcttggct tgaatttggg cagaagggtg gtgccaaag gaaatgtaca atgtctgaga     480
aaaattctta ttcaactaac aattacccag atctgtatgg ccccactagg cactgttcct    540
ggagctttgt gtacatctcc cactgaaaat gcagtgggaa gctttatgat gatgcctact    600
ttgcaggtgt ttcgatgact ctgggtggtt taagtgactt tccaaagtca cagagataat    660
aaggcataga cttgggataa gatcccaggc ttctgacatg gaaaaaagca ggtcacaagg    720
atttgcggtg ttagaagaac agcagctgta gcgtctgcct gccagtgtgc cttgagttga    780
cactgtccac aacaagtact ggaaggcagg agagggagg tcctatgtaa gtttccttgg     840
cctttagaag aaaccctgtg tccaggctct ctgtcaacta agtcacatat cgaactgggg    900
caggtagtga tatatggcta attaaatgtg ccatgtaaac aatatctgac cactaatttt    960
aaaaaacagt ttgtaaaaca ttcctggcat catttaatct tttggggttt tcgcttgttg   1020
tattcagaag gtattttagg accaacctta attgtcatgc attcattcaa cgaatattta   1080
ttaacctacc tactgtgttg tatccagcac tgttttgttt tgttgttgtt tgttttttg    1140 gggacagaat ctcactctgt tgcctagggt ggagtgcagg gcacaatat ctgctcactg     1200 caacctccgc ctcctgggtt caagcgattc ccgtgcctca tactcccaag tagctgggat    1260
tacagttgtg cgcagcaact gctcagctaa ttttcgtatt tttcatagag acagggtttc   1320
accttgttgg ccaggctggt cttgaactcc tgacctcagg tgatcctccc gccttggcct   1380
cccaaattac tgggattaca ggtgtgaccc actgcgccca gccataaaac tctttaacac   1440
aaactcttca aagtgacatc ttttgtaacc ttcataggtt acaaaggta ttgatatatt     1500 aacagattga gatttgattg cggggggggcg gggcagggg agaatgctaa aaaaataagt    1560
```

```
cagctttctt ttctgtaact atttaaaaga atgcaaagta attctacagg caattccttg   1620
gtgggcttat ttggtaattt ttttttttctt ttccattttc ctcttgctct ttggtttgta   1680
ggagaaccgc tttattccca ggaggcaatt ttgagtccca acatgtcctg catcatctcc   1740
tgtgcccatt gccaaaggaa ggcgaccaga gcgtgggttt cagcacagct ctgattggat   1800
gataagcaag gagagtaata atgctgctag gaggttagag aaaagaaaat actagaatat   1860
accagaatgt agtgtttcca cttccctccc tccaaatcaa aagcctcatg aatgaaatta   1920
tgaccattat tcaagtgcaa ttatactgag tatgtaaaat ggaaacactg aaagtaaatc   1980
atacatttgg atattacatt tcatatttga gaacatgcca gaaacattgt attattgttg   2040
agtgtaatgt caggagacaa acttctacgc attttataca taaattttc cattttctct    2100 gtttcccatt tatgtcaagt tgaacacatg gtatgacttt taatattctc tcttccttct   2160
ccttccccac attgaatgtc aagtgatcac actcaatctt gattatccta aatttaccct   2220
taggacctgt caccccattg ggtgttgccg ccagaacaag agggtttttt aattggtata   2280 aaaggagag gccaggcttg gtagctcatg cctgtaattc tagcactttg ggaggctggg    2340
gcgggaaatc ccttgatccc aggagtttca gaccagcctg gcaacatgg tgagactctg    2400 tctctataaa aaaaaaaatt ttttttttta atttagctgg gtgtggtggc atgccctgta   2460
gtctcagcta ctatggaggc tgaggtggga ggatcacttg atcctggaag gtggaggctg   2520
cagtaagctg agtggcacca gtgcactcct gtcaaaagag agagaggaga gagagagaga   2580
gaaagaggaa gagtccctaa agaaacctat aaaactgggg tcttatggat gctagcaaca   2640
tatcttggaa agaactgcca gcgccagtgg attacagaag acaactgtgg ctacaggctg   2700
ttcttgccag ctcaggcgtc aactcgtgga aaccggttaa tgacccgagg ggacagcgga   2760
ttctcgccta agcaagatcc cgcagatggg agggcgtagg aagaggttcc ccgggccggc   2820
tccaggcccc agcgggcgtg ggcgttggca gtgagcgagg ggtggtcccg cgccgcgccg   2880
gcggggggcg cccgaatgag agcgcggggc ggtgccgttg ggaccacggc ggccagagcg   2940
gcaggatggc ttccggcttc aagaagccca gcgctgcctc caccggccaa aagagaaagg   3000
tggcacctaa gcccgagctc actgaggatc agaagcaaga agttcgggaa gcatttgacc   3060
tcttcgacgt ggacggaagt gggaccatcg acgcgaagga gctgaaggtg gccatgagag   3120
cgctggcttt cgaacccagg aaggaagaga tgaagaaaat gatctccgag gtggacaggg   3180
aaggcacggg gaagatcagc ttcaatgact tcctggccgt gatgacgcag aagatgtccg   3240
agaaggacac caaagaagaa atcctgaagg ccttcaggct cttttgatgac gatgagaccg   3300 ggaagatctc gttcaaaaac ctgaagcgtg tggccaacga gctgggggag aacctcacgg   3360
atgaggagct gcaggagatg atcgacgaag ctgatcggga tgggacggc gaagtgaacg    3420 aggaggagtt ccttcggatc atgaagaaga ccagccttta ctgaagtcgg ttcagaagct   3480
aaagtgactc tctgggttgc ctgcttccat tttgtgaaac cttagaggac agcggctgcc   3540
tgtcccttct tcaccccctc accccataa tttgtctaga tctatttcca tatctctagt    3600
tcaataatag aatttgaaag atgcttgtaa tgtgagtttt gggttttaat tctcaagagt   3660
caacctggag cacatgaggt taaacaaagg gccctgaagt ttgagtgcgc cctccatttg   3720
ccctgtgctg aacttgctgt tcatctgttg atctggaggc aggacagctt ctgggacaca   3780
caaaaatgtg gttccctttg tcacttcttt ggtggtctta aattatcttg cttcatatat   3840
cattccttaa attccagtca ttgttccagc ataatgagat ggaatctgcc agtagatttg   3900
```

```
cctagcctgt ccacttagct gaataccagt ttgaaggaaa acagggtggc cacttacaaa    3960
cttacggagc tcaggacaga taatcttata aagaatagac ttgcttgggt ggtagtacgt    4020
tgtgcaattt tgactattca ctggctttat acctgcaaat gattcttcgt tcatgtgtaa    4080
attgtccacc atgggtttat ctagggctag tatgtatacc tgggctacag aataaaaata    4140
aaatctaata ctggcccaag caaagtataa tttgcttaag aggttacgct aacaaacgat    4200
tttgagtaaa tatttacaaa tgtaggatct tagtttagga aattataaca ataccttaa     4260
tataacattt taagctactt atagtccttg gaaatagcaa caaatatctt agttattgga    4320
ctattataac cttagtcatc ttattactgc ttgattatga cactctcc ctgctaatcc      4380
ttagaacatc ttggttcttg gtacttgact tttagcccct ctgacatata gttgatgtca    4440
gagtgtctgg catttcagta gtgctctatt ttacaaatcc cagtaaactg ctccactgtg    4500
gcttgtttat gtgttaatac tgcttgtttt ctgttataaa ttatttttg ctttggagta     4560
agatatcatc attttgcata gctacaaatc tgaagttaaa gaaaatttta aaaatgtaat    4620
tgtgggaaaa taacaaatag atctgctgag atggaggctt tgactaatgt tttaataaca    4680
ggcaacaaaa caaagaggca ggatattttg gtcacaacta aacctaaatt aaatcctcat    4740
acaaagcccc attaagataa atgctcaaat tctgggaaca tttcacttgc tttgccagca    4800
attttacccct tcagagggtg tggatctaat caggggaaca aactaccctg ggcttaattc    4860
tcattaacag ggactaattt gtcaaagcgg cagtactagc tgaagtgatg ggtatggaag    4920
cattcactgt gaggattttg ctgaggtgcc tggcacaggg tagggaact cacccaggct     4980
gcaagatgct aacagttcag gttcaaggtc ttagtgtgga ctaaggtgca gtcaggatgg    5040
gaacaggtgc aacttgggcc aacatcagta tgaagggcct gatctgaggg caggggaagg    5100
aggggggcatt ctgggaagca agagttcctg gtatcctgtt gaccagagtc ttggcccaag   5160
gatcaacgta tgaattaaag tagaaatacc agaaacaaag aaagttggca gaaactagga    5220
gaagcagagt ctcagccaac tggactgggc tcagccttgg ctactggccc ggcagatgat    5280
agaagagaaa accaggaacc caggctgaag cccagtggtt gggctggcca cacaccatgc    5340
atagccttaa aggggtggcc taagggcatg gtccgctcca aaaaggaaa gggggcccca     5400
gaatatttct gaatcccact cactgccagg gaagaacctc tcaattcact caatagtgca    5460
ttctcctgct tctcaatagg ctaatactct agagaatatg gggacaaggg gaggagggtc    5520
tagtggaaca ggtctaaact ggcgtttgaa ttttaagata agttaatcat acattggctg    5580
ggtcagccat gtctcttagt ctttacaaaa gtagaacaca aaaaaattca atggaaatct    5640
acagacacct atttgcagat gaggaaacac ggctatgaag attgggaaga ttgggaagaa    5700
ctggccaggt gtggtgctca cgcctgtaat cccagcactt gggaggccg aggctggtgg     5760
atcacttgag gtcaggagtt ggagaccagc ctgggcaaca tagtaaaacc ctgtctctac    5820
tcaaattaca aaaatcagca gggcgttgtg gtgcccacct gtaatcccag ctatgcagga    5880
ggctgaggca ggacaatcac ttgaacctgg taggcggagg ttgcagtgag ccaaaatcac    5940
gccactgtac tccagcctgg gtgacagagc aagactttgt taaaaaaaa aaaaaaaag     6000
ggaagaacta aaaatgtaat tttcaagggg ctatcacaaa tggtcccaat aaagagaaag    6060
caggactcat gtttaagaaa cccatgagat gtgtatggac ctcatggaag agctcttgct    6120
ttctaatgat ctacgtaaca gatgaaaagc agagcatagg gctaaggatg aaaatacaac    6180
agtaataagg tattaatata ttattaagaa agctaatgct ccacataagc agaggacatt    6240
aaagggactt ttttttctta aggatatctt aatgttttaa atgagaagac atagaaaggg    6300
```

```
ataggtccaa ctcttgggat tgttgcaggt tggtttccat cggaagcact ctgagtctga      6360
gatttgtatg cagaaaatta atttgaatgt gcttttcaga tcacccaggt gggggaggga      6420
ggaaaccagg actgggcaga gagaggctgg gctgtaacca agtcacaaca aaggtgtcag      6480
ctggtcccat ggtgaattct ggacctagga tggctgatcc caaggcattc caaactgggg      6540
caaggaagtt gtgctttaaa acttctcatt gactgtcagt cactgggcat gagcagtccc      6600
caggaagggg ggatgacctt gagcaaggtg gatgtcttca gccaagggca atcactggga      6660
aggagaaccc agctatgaac tgtcagctgc caacactccc agcatctga                 6709
```